US011617853B2

(12) United States Patent
Alizoti et al.

(10) Patent No.: US 11,617,853 B2
(45) Date of Patent: Apr. 4, 2023

(54) NASAL MASK WITH AROMATIC DISPENSER

(71) Applicant: Trudell Medical International, London (CA)

(72) Inventors: Neritan Alizoti, London (CA); George Baran, London (CA); Darlene Haapanen, London (CA); Mark Nagel, Mt. Brydes (CA); Jason Suggett, London (CA)

(73) Assignee: TRUDELL MEDICAL INTERNATIONAL, London (CA)

( * ) Notice: Subject to any disclaimer, the term of this patent is extended or adjusted under 35 U.S.C. 154(b) by 531 days.

(21) Appl. No.: 16/696,547

(22) Filed: Nov. 26, 2019

(65) Prior Publication Data

US 2020/0197654 A1  Jun. 25, 2020

Related U.S. Application Data

(60) Provisional application No. 62/773,759, filed on Nov. 30, 2018.

(51) Int. Cl.
*A61M 21/00* (2006.01)
*A61M 16/06* (2006.01)

(52) U.S. Cl.
CPC ............ *A61M 21/00* (2013.01); *A61M 16/06* (2013.01); *A61M 2021/0016* (2013.01); *A61M 2210/0618* (2013.01)

(58) Field of Classification Search
CPC .............. A61M 11/04; A61M 15/0003; A61M 15/0018; A61M 15/0086; A61M 15/009; A61M 16/06; A61M 16/208
See application file for complete search history.

(56) References Cited

U.S. PATENT DOCUMENTS

| 5,243,972 A | 9/1993 | Huang |
| 5,265,595 A | 11/1993 | Rudolph |

(Continued)

FOREIGN PATENT DOCUMENTS

| CN | 208355894 U | 1/2019 |
| CN | 110141744 A | 8/2019 |

(Continued)

OTHER PUBLICATIONS

PCT Notification of the International Search Report and Written Opinion of the International Search Authority for Application No. PCT/IB2019/060202, dated Feb. 18, 2020, 10 pgs.

(Continued)

*Primary Examiner* — Christine H Matthews
(74) *Attorney, Agent, or Firm* — Crowell & Moring LLP

(57) ABSTRACT

A mask includes a body having an interior surface defining a cavity shaped to receive a user's nose. An exterior surface of the body is exposed to an ambient environment. The body includes an inlet in fluid communication with the cavity and a one-way exhaust valve in fluid communication between the cavity and the ambient environment. A therapeutic substance dispenser is in fluid communication with the cavity. In one embodiment, a nasal aromatic decongestant is disposed in the therapeutic dispenser. A mask includes an upper nasal cavity separate from a lower oral cavity, with an inlet in fluid communication with only the upper nasal cavity. A medicament delivery assembly, and methods for the use thereof, are also provided.

21 Claims, 21 Drawing Sheets

(56) References Cited

U.S. PATENT DOCUMENTS

| | | |
|---|---|---|
| 5,701,886 A | 12/1997 | Ryatt |
| 6,336,453 B1 | 1/2002 | Scarrott et al. |
| 6,904,908 B2 | 6/2005 | Bruce et al. |
| 7,360,537 B2 | 4/2008 | Snyder et al. |
| 8,151,794 B2 | 4/2012 | Meyer et al. |
| 9,700,688 B2 | 7/2017 | Engelbreth et al. |
| 2009/0293881 A1* | 12/2009 | Graham ............... A61M 16/06 128/207.12 |
| 2010/0101570 A1 | 4/2010 | Meyer et al. |
| 2017/0119986 A1 | 5/2017 | Poree |
| 2018/0000696 A1 | 1/2018 | Villeneuve et al. |
| 2019/0336717 A1 | 11/2019 | Hickey et al. |

FOREIGN PATENT DOCUMENTS

| | | |
|---|---|---|
| DE | 4004157 C1 | 4/1991 |
| DE | 4219535 A1 | 10/1992 |
| EP | 3 360 477 A1 | 8/2018 |
| GB | 2 385 533 B | 8/2005 |
| JP | 80164207 | 6/1996 |
| JP | 2706052 | 10/1997 |
| WO | WO 2014/105060 A1 | 7/2014 |
| WO | WO 2015/186124 A1 | 12/2015 |
| WO | WO-2018033863 A1 * | 2/2018 ............ A61M 11/00 |
| WO | WO 2019/051612 A1 | 3/2019 |
| WO | WO 2019/178693 A1 | 9/2019 |

OTHER PUBLICATIONS

Pederson, W. et al., "Nasal inhalation of budesonide from a spacer in children with perennial rhinitis and asthma", *Allergy*, vol. 54, 1998, pp. 383-387.

\* cited by examiner

NASAL MASK WITH AROMATIC DISPENSER

This application claims the benefit of U.S. Provisional Application No. 62/773,759 filed Nov. 30, 2018 and entitled "Nasal Mask With Aromatic Dispenser," the entire disclosure of which is hereby incorporated herein by reference.

TECHNICAL FIELD

The present invention relates generally to a mask, and in particular to a nasal mask with an aromatic dispenser, and also to medicament delivery assemblies and methods of delivering aerosol medicament or the like.

BACKGROUND

It is well known to deliver aerosolized medicaments to a patient via various devices, including nebulizers and aerosol dispensing devices, such as pressurized Metered Dose Inhalers (PMDI's), in order to treat various conditions and diseases, including but not limited to various respiratory conditions and diseases such as asthma. In some embodiments, the patient interface is configured as a mask, which typically is fitted around the nose and mouth of the user so as to maximize and ensure inhalation of the aerosolized medicament into the lungs of the user. Such masks, however, may not ensure treatment of the upper respiratory airways. Treating only the lower respiratory airways may not be sufficient to treat the entirety of the symptoms, for example diseases residing in the upper respiratory airways. In addition, such masks may have a relatively large dead space.

SUMMARY

Briefly stated, in one aspect, one embodiment of a mask includes a body having an interior surface defining a cavity shaped to receive a user's nose. An exterior surface of the body is exposed to an ambient environment. The body includes an inlet in fluid communication with the cavity and a one-way exhaust valve in fluid communication between the cavity and the ambient environment. A therapeutic substance dispenser is in fluid communication with the cavity. In one embodiment, the therapeutic substance dispenser is in fluid communication with the cavity at a location spaced apart from the inlet, for example through an orifice. In another embodiment, the dispenser is in fluid communication adjacent the inlet. In one embodiment, a nasal aromatic decongestant is disposed in the dispenser. In one embodiment, the exhaust valve is omitted.

In another aspect, one embodiment of the dispenser includes a receptacle defining a second cavity. A cover is movable between a use position, wherein the second cavity is in fluid communication with the orifice, a storage position, wherein the second cavity is not in fluid communication with the orifice, and/or a loading position, wherein the receptacle is open to the ambient environment. In one embodiment, the receptacle is not open to the ambient environment when the cover is in the storage position.

In another aspect, one embodiment of a medicament delivery assembly includes a medicament delivery device coupled to the inlet of the mask. The medicament delivery device may include for example a holding chamber, configured with a pressurized metered dose inhaler, or a nebulizer.

In another aspect, one embodiment of a method of delivering an inhalable substance includes positioning a nose of a user in a cavity of a mask, wherein the mask comprises an inlet and a one-way exhaust valve, disposing a therapeutic component in fluid communication with the cavity, inhaling through the nose positioned in the cavity, introducing an inhalable substance into the cavity through the inlet of the mask, drawing the inhalable substance from the cavity into the nose, entraining a therapeutic substance while inhaling through the nose and drawing the therapeutic substance into the nose, exhaling through the nose into the cavity, and opening the one-way exhaust valve in the mask while exhaling. In some embodiments, the user may exhale through their mouth, or through an exhaust valve in a medicament delivery device.

In another aspect, one embodiment of a mask includes a body having a barrier separating an upper nasal cavity shaped to receive a user's nose and a lower oral cavity adapted to be in fluid communication with the user's mouth. An exterior surface of the body is exposed to an ambient environment, with an inlet in fluid communication with only the upper nasal cavity. A one-way exhaust valve is in fluid communication between the lower oral cavity and the ambient environment. In one embodiment, a second one-way exhaust valve may be in fluid communication between the upper nasal cavity and the ambient environment.

The various aspects and embodiments provide significant advantages over other masks, delivery assemblies and methods. For example and without limitation, the mask and assembly provide for treating both the upper and lower respiratory airways. Moreover, drug delivery at the nasal cavity allows for larger aerosol droplets to be deposited first, with finer/smaller aerosol droplets being deposited downstream in the lungs, thereby treating both target areas at the same time.

In addition, the mask, which may be configured as a nasal mask, or with an upper nasal cavity, minimizes the dead space within the mask while achieving a good seal around the nose and face and accommodating most typical nose sizes. The ability to introduce a therapeutic substance, such as a nasal aromatic decongestant, further enhances the treatment process by enhancing the user's smell sensation and delivering a decongestant, thereby providing better drug delivery, providing decongestion, and improving the overall user satisfaction. Moreover, in one embodiment, the therapeutic substance may be administered first, thereby opening up the airways prior to administering the drug/medicament.

The present embodiments of the invention, together with further objects and advantages, will be best understood by reference to the following detailed description taken in conjunction with the accompanying drawings.

BRIEF DESCRIPTION OF THE DRAWINGS

FIGS. 7A and B are perspective views of another embodiment of a mask in solid and see-through configurations, while

FIGS. 10A and B are a perspective and side views of another embodiment of a mask, while

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" cavities may refer to any sequence of such features, and is not limited to the first and second cavities of a particular configuration unless otherwise specified. It should be understood that the terms "input end," "output end" and "inlet" refer to the function of those features during an inhalation phase, and that the inlet may serve the opposite function (removal or exit) during an exhalation phase. The phrase "fluid communication" refers to the ability of a fluid, whether a gas or liquid, to flow or pass from one component or feature to another component or feature, including intermittently, for example when a valve is open to permit such flow. The phrase "ambient environment" is the environment or atmosphere, e.g. air, surrounding the component or feature, including for example the mask. As used herein, the term "upstream" refers to the direction from which a flow of gas is originating while the term "downstream" refers to the direction toward which the flow is traveling, for example, during inhalation, air flows from an upstream medicament delivery device to a downstream user.

Figure 10A:
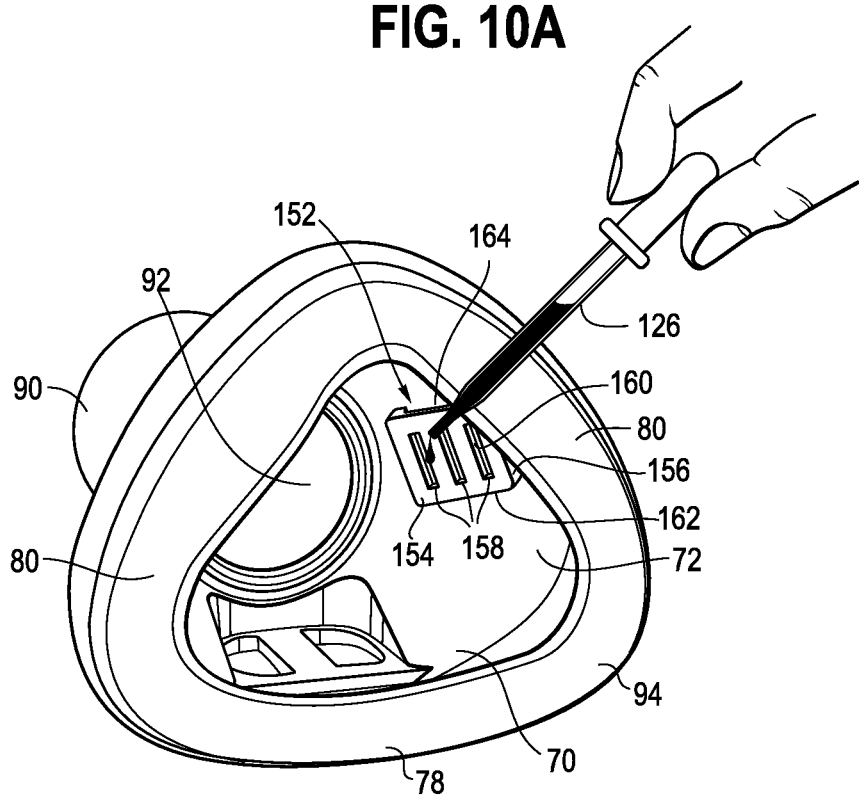
Figure 10B:
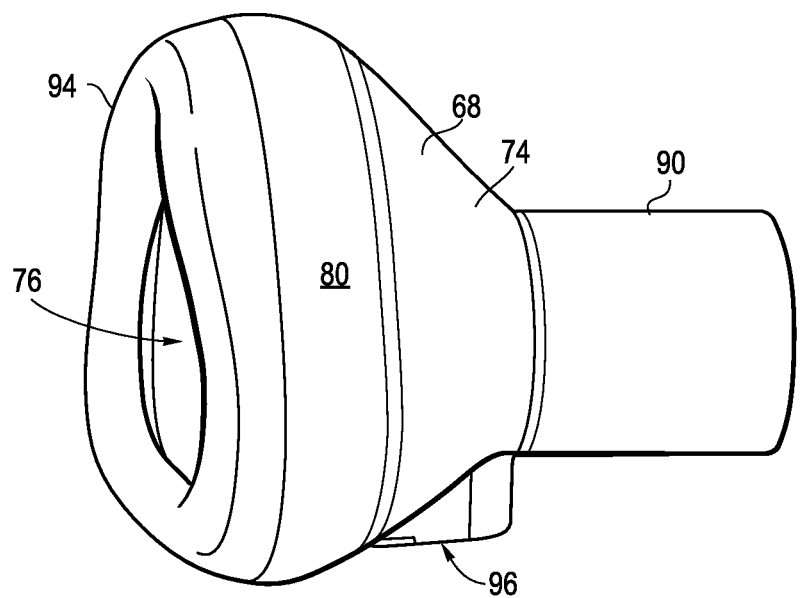
Figure 10C:
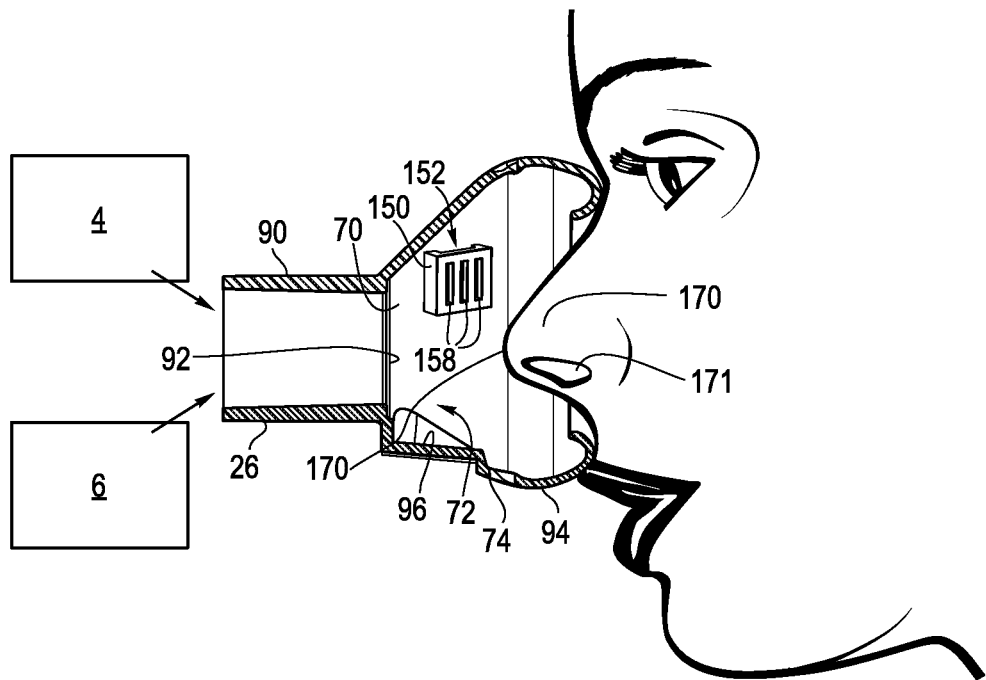
FIG. 10C is a side view of mask in use.
Figure 11:
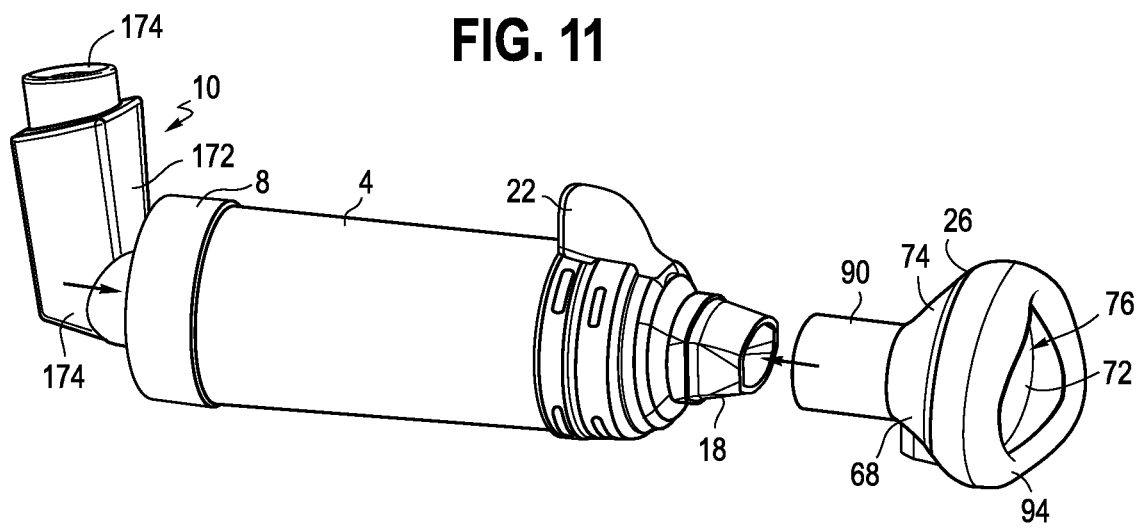
FIG. 11 is an exploded view of a medicament delivery assembly.

Referring to FIGS. 1-3 and 17A and B, various medicament delivery assemblies 2 are shown as including a medicament delivery device, configured for example as a holding chamber 4 in one embodiment. The medicament delivery device may alternatively be configured as a nebulizer 6 as schematically illustrated in FIG. 10C. The holding chamber may have various antistatic properties. The holding chamber has an input end 8 configured to mate with a delivery device 10, such as a pressurized metered dose inhaler. The holding chamber further includes an output end 12 configured with a baffle 14 and a one-way inhalation valve 16 in one embodiment. The output end 12 may further include an annular flange 18 or tube, configured as a mouthpiece in one embodiment, which is shaped to engage and support a user interface. The holding chamber may be configured with a visual indicator 22 that provides visual indicia when the user is exhaling and/or inhaling. Various suitable holding chambers are disclosed in U.S. Pat. Nos. 6,336,453, 7,360,537, 6,904,908, the entire disclosures of which are hereby incorporated herein by reference. The holding chamber may further include an input end that is suitable for connection to a ventilator circuit or other oxygen supply. Such holding chambers are further described and disclosed in U.S. Publication No. 2010/0101570 and U.S. Pat. No. 8,151,794, the entire disclosures of which are hereby incorporated herein by reference.

Figure 1:
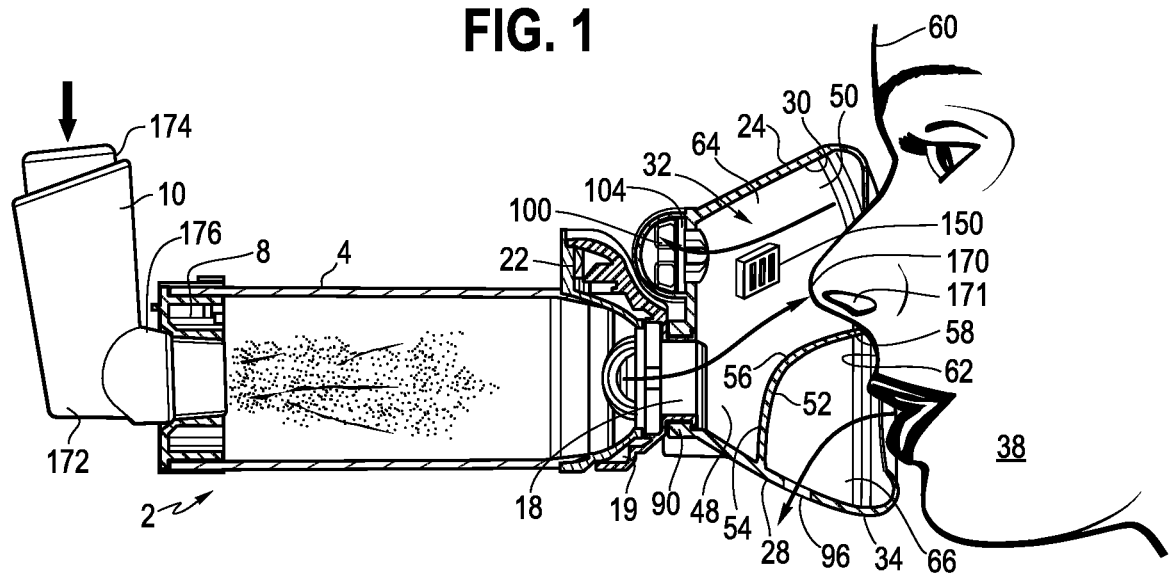
FIG. 1 is a partial side cross-sectional view of one embodiment of a medicament delivery assembly in use.
Figure 2:
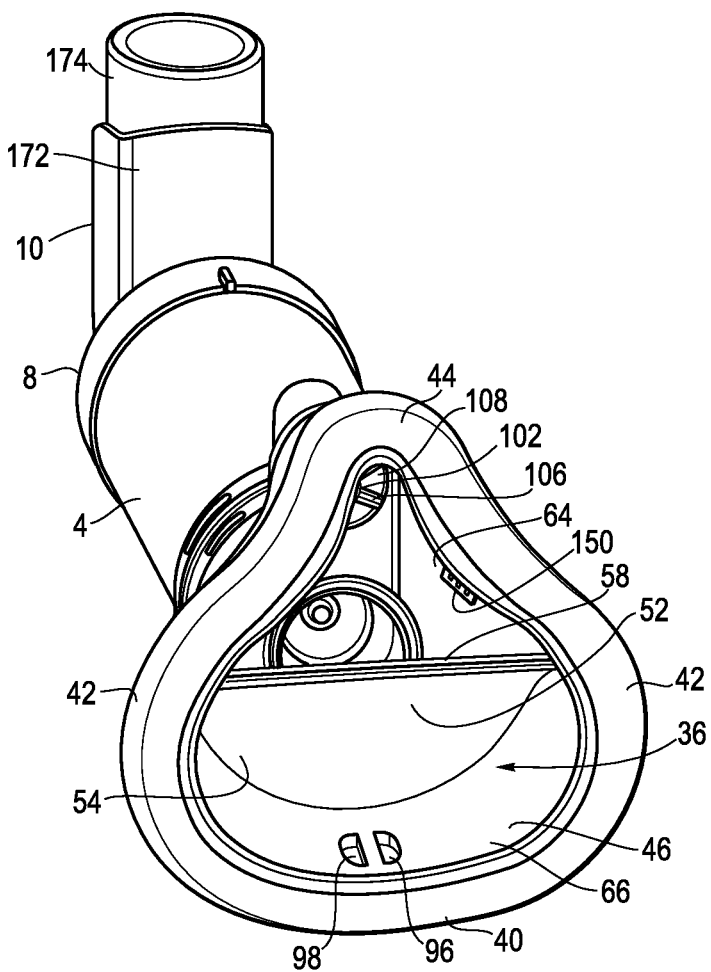
FIG. 2 is a perspective end view of the medicament delivery assembly shown in FIG. 1.
Figure 3:
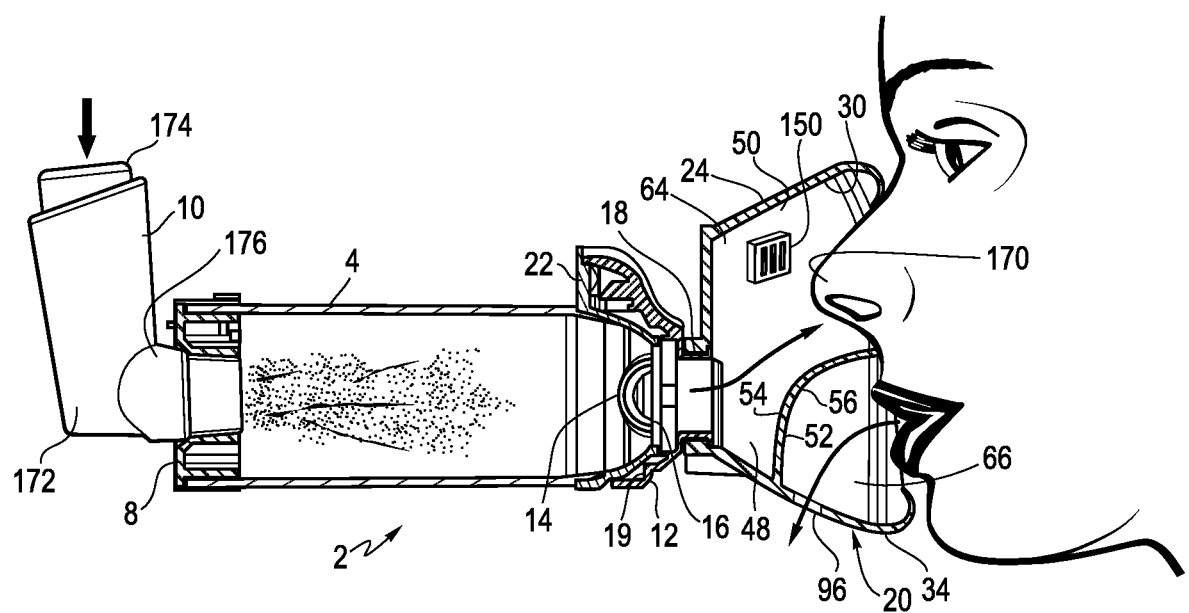
FIG. 3 is a partial side cross-sectional view of another embodiment of a medicament delivery assembly in use.

As shown in FIGS. 1-23, the user interface 20 is configured as a mask 24, 26, 200. In one embodiment, shown in FIGS. 1-3, the mask 24 has a body configured with an outer shell 28 having an interior surface 30 defining a cavity 32 and an exterior surface 34 exposed to an ambient environment. The body defines an opening 36 shaped to receive the face 38 of a user. In the embodiment of FIGS. 1-3, the opening has a tear-drop shape, with a curvilinear bottom edge 40 and curvilinear side edges 42 extending upwardly from the bottom edge and meeting at a narrowed apex 44. The shell has a corresponding wall defining the cavity, including a bottom wall portion 46 that transitions into opposite curved side wall portions 48 and an upper curved wall portion 50 defining the apex.

A barrier 52 has an upwardly extending vertical portion 54 that extends upwardly from bottom wall portion 46 and spans between the opposite side wall portions 48, and a forwardly extending horizontal portion 56 spanning between the opposite side wall portions 48 and terminating at a user interface edge 58 positioned adjacent a plane 60 defined by the bottom and side edges. The interface edge 58 is positioned to engage, or be disposed adjacent to, a user's upper lip 62 as shown in FIGS. 1 and 3. The barrier 52 separates the cavity 32 into an upper nasal cavity 64 and a lower oral cavity 66, with the barrier precluding fluid communication therebetween, except as may transpire between the edge 58 and the upper lip 62. The barrier 52 thereby helps minimize the dead space in the upper nasal cavity 64.

Figure 12:
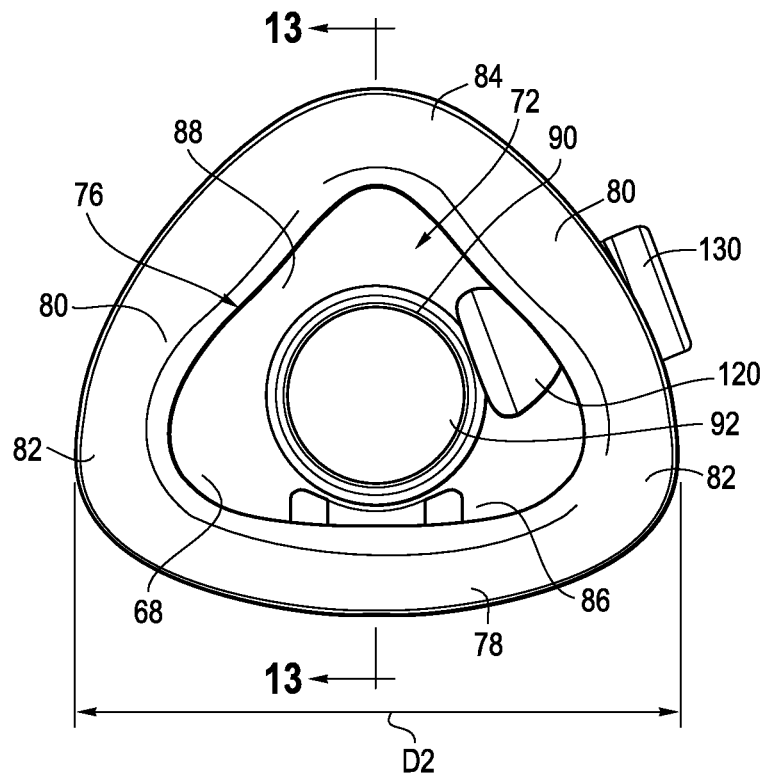
FIG. 12 a front view of one embodiment of a mask.
Figure 13:
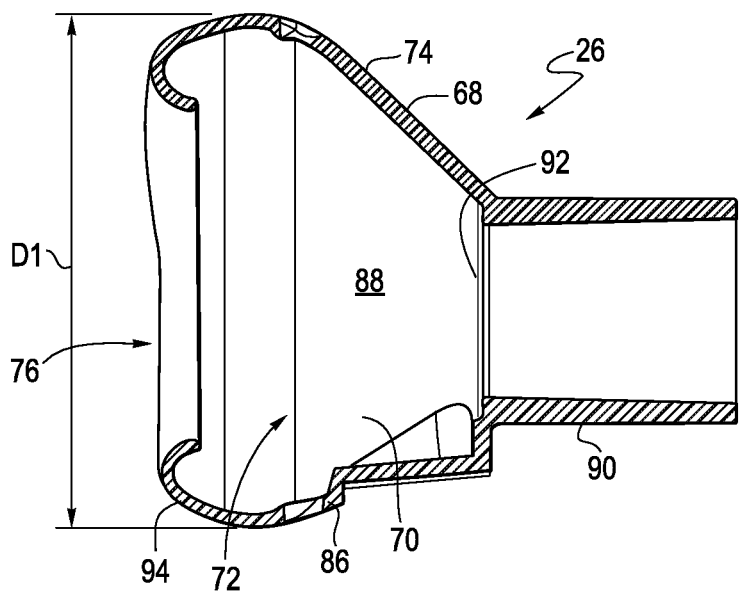
FIG. 13 is a cross-sectional view of a mask taken along line 13-13 of FIG. 12.
Figure 14:
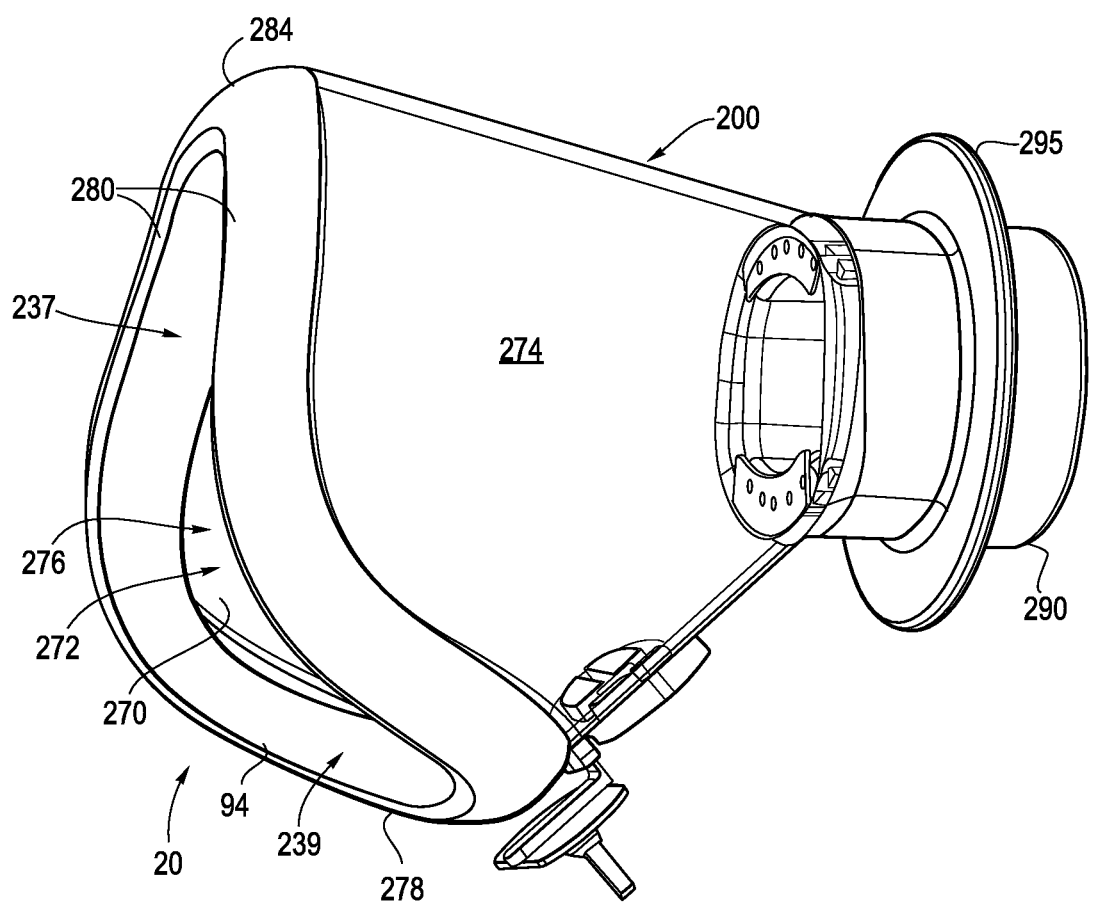
FIG. 14 is a perspective view of another embodiment of a mask.

Referring to FIGS. 4A-23, the mask 26, 200 is configured as a nasal mask having a body configured with a shell 68, 268 having an interior surface 70, 270 defining a cavity 72, 272 and an exterior surface 74, 274 exposed to the ambient environment. The cavity is relative small and minimizes the dead space associated with the mask. The body defines an opening 76, 276 shaped to receive the nose 170 of a user. The opening has a generally triangular shape, with a curvilinear bottom edge 78, 278 joined to curvilinear side edges 80, 280 at corners 82, 282 and extending upwardly from the bottom edge and meeting at an apex 84, 284. The shell has a corresponding wall defining the cavity, including a bottom wall portion 86, 286 defining the cavity that transitions into opposite curved side wall portions 88, 288. The user's nose 170 fits in the opening 76, 276, with the nostrils 171 extending past the bottom edge 78, 278 into the cavity 72, 272 formed in the mask. The apex 84, 284 fits over the top of the patient's nose. As shown in FIGS. 12 and 13, in one embodiment, the distance D1 between the top and bottom of the mask is between and including 60 mm to 90 mm, while the distance D2 between the bottom corners 82, 282 of the mask is also between and including 60 mm to 90 mm, meaning the mask has an perimeter with a generally equilateral triangular shape, albeit with a curved sides, bottom, corners and apex.

Figure 15:
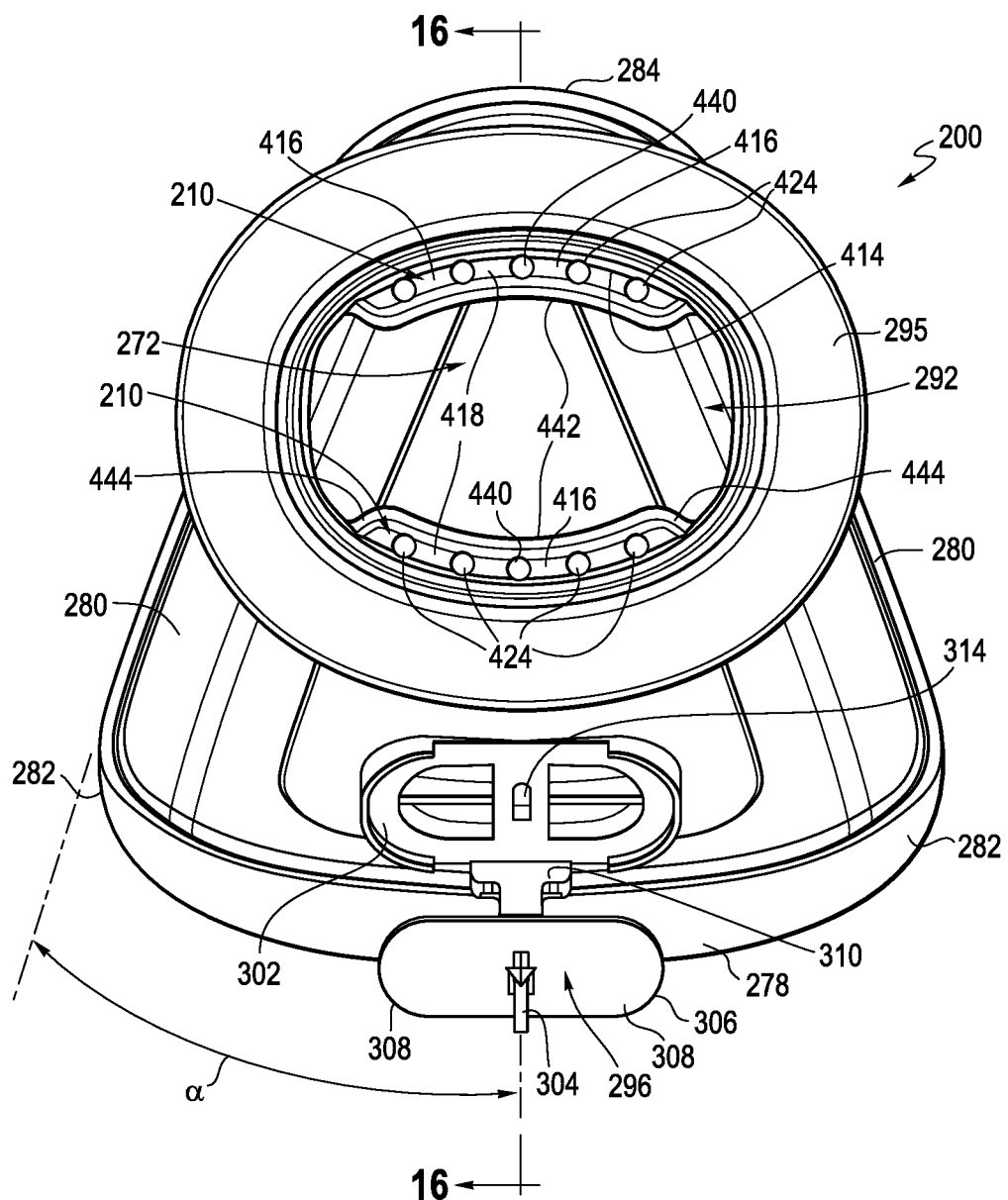
FIG. 15 is an end view of the mask shown in FIG. 14.

In the embodiment of FIGS. 14-23, the opening 276 has forwardly facing upper portion 237, and a downwardly and forwardly facing lower portion 239. In this embodiment, the bottom edge 278 extends rearwardly from the side edges 280. The upper portion 237, and the side edges thereof, define a face or plane that is angled slightly relative to a vertical plane, for example at 9 degrees, with the longitudinal axis of the holding chamber defining a horizontal axis. The lower portion 239, and the bottom edge thereof, define a second plane that is angled relative to the vertical plane, for example at 60 degrees, such that the planes defined by the upper and lower portions 239, 237 define an angle therebetween of 111 degrees. In other embodiments, the upper portion may define a vertical plane, or be angled forwardly from the vertical plane, or angled rearwardly at other angles for example between 0 and 20 degrees. The second plane of the lower portion may also be angled at other angles relative to the vertical plane, for example between 45 and 75 degrees. The bottom edge 278 engages an upper lip of the user, or the portion of the user's face between the mouth and the nose. The side edges 280 may be angled relative to a centerline axis at an angle α, which may be between 15 and 25 degrees, and more preferably between 19 and 21 degrees, as shown in FIG. 15. As noted, the shape of the mask minimizes the dead space volume inside the mask, while also providing a periphery that comfortably mates with the face of the user.

Figure 16:
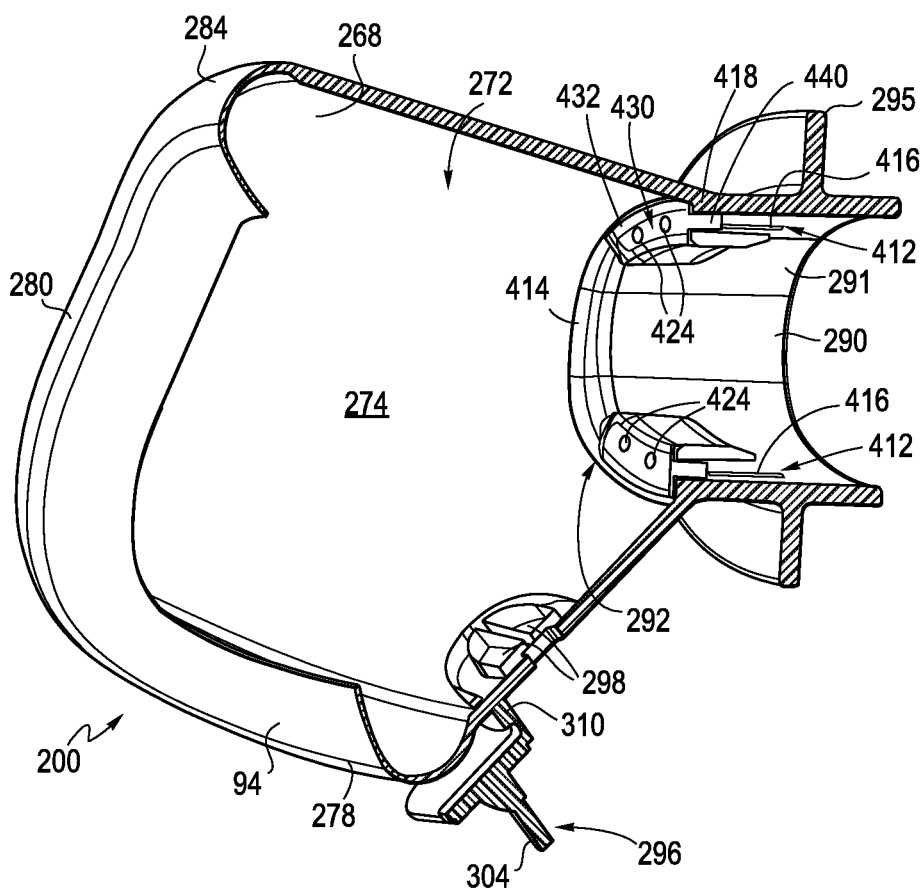
FIG. 16 is a cross-sectional view of the mask shown in FIG. 14 taken along line 16-16 of FIG. 15.
Figure 17A:
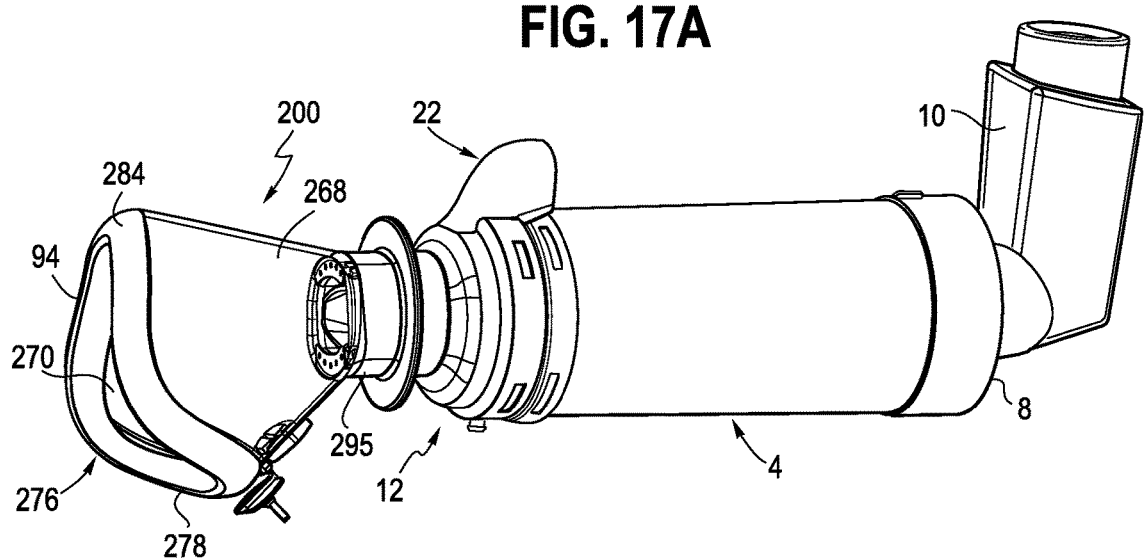
FIG. 17A is a side perspective view of the mask shown in FIG. 14 coupled to a valved holding chamber.
Figure 17B:
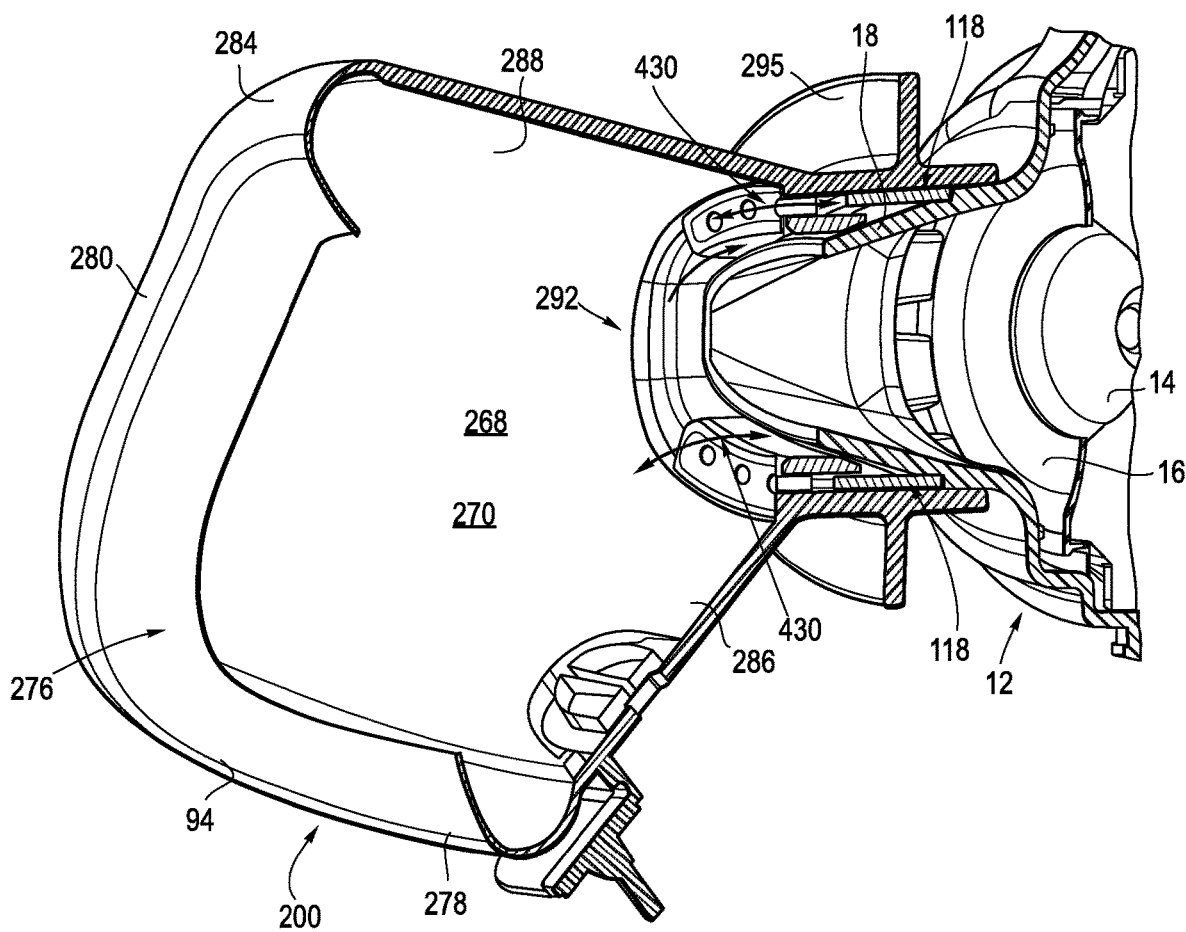
FIG. 17B is an enlarged view of the mask and output end of the valved holding chamber shown in FIG. 17A.
Figure 18A:
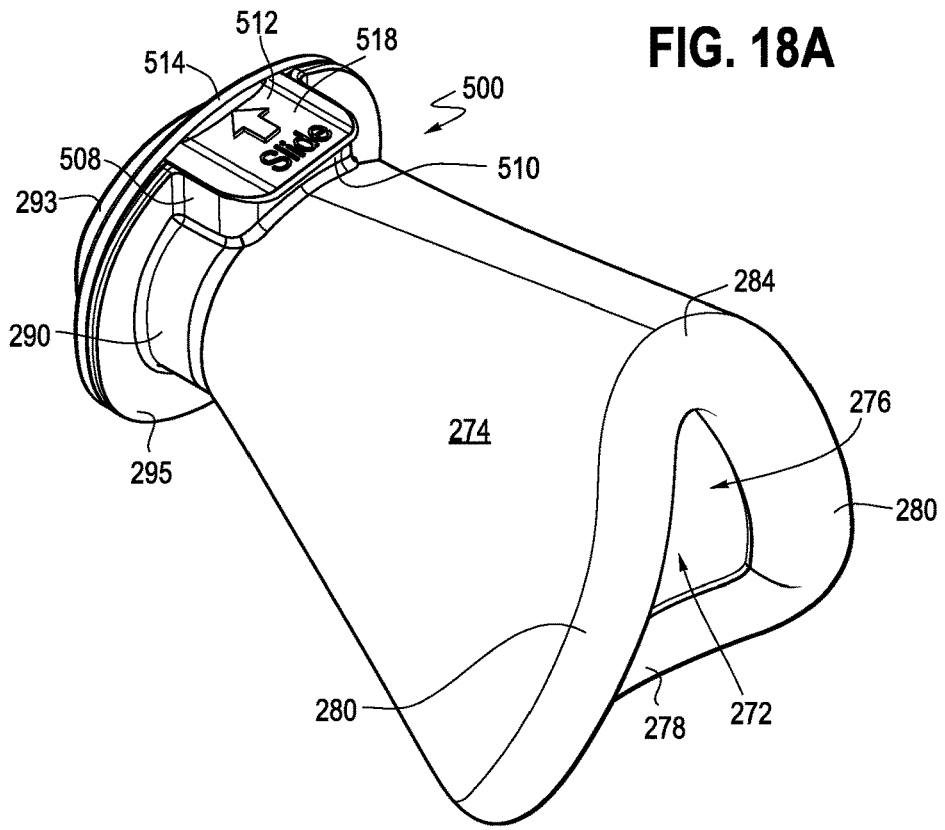
FIGS. 18A and B are perspective assembled and exploded views of another embodiment of a mask.
Figure 18B:
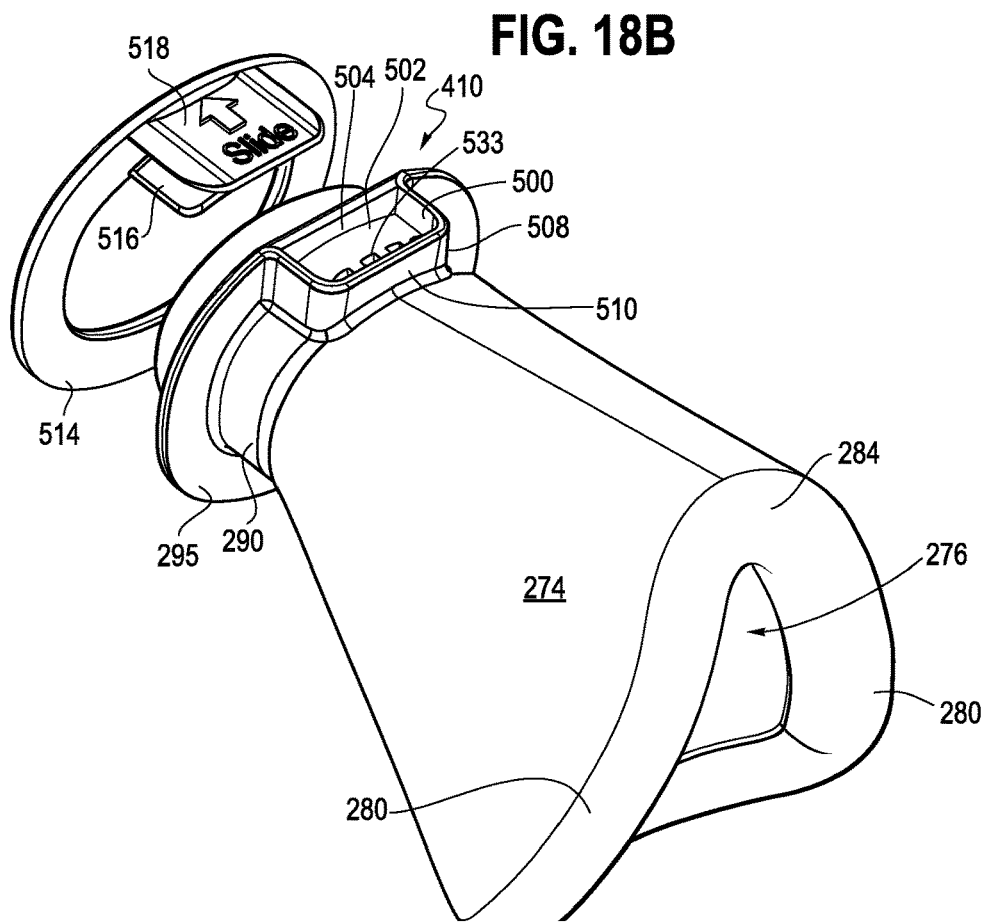
Figure 19A:
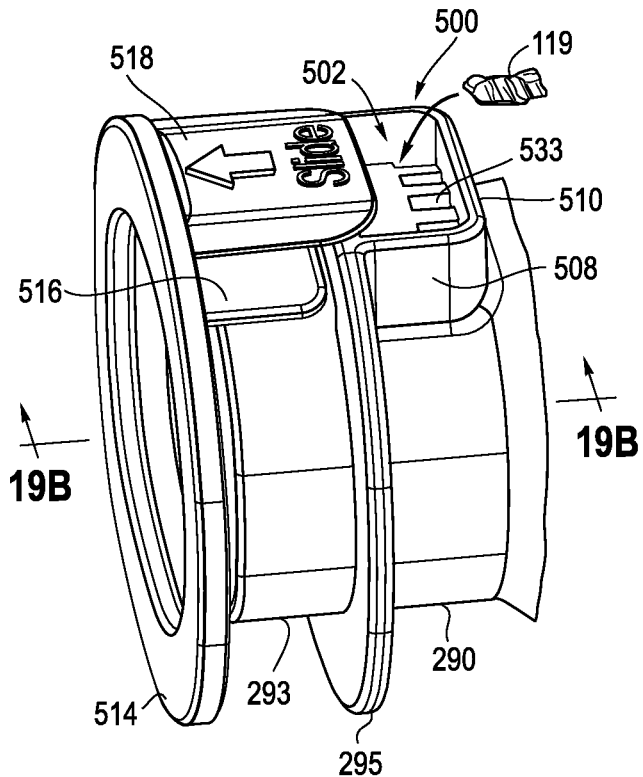
FIGS. 19A and B are side and cross-sectional views of a portion of the mask in a loading configuration.
Figure 19B:
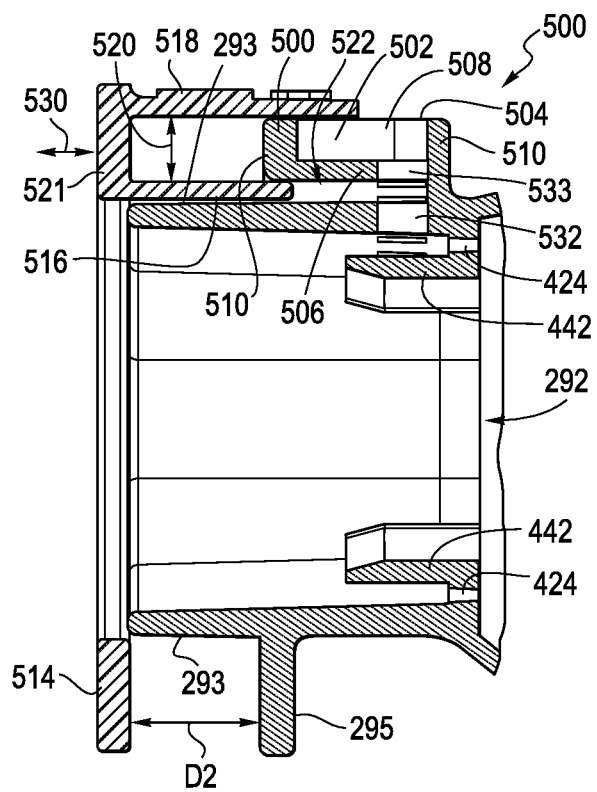

In all embodiments of FIGS. 1-23, the mask 24, 26, 200 includes an annular mounting flange/tubular mounting portion, or tube 90, 290, shaped and configured to receive the end portion 18 of the holding chamber or other substance delivery device, whether by being inserted in the end portion 18 or by surrounding the end portion 18. For example, the tube may 290 have an obround or elliptical cross section, or the tube may be cylindrical with a circular cross section. The tube 90, 290 defines a flow channel between the holding chamber and cavity 272 through which an inhalable substance, such as an aerosolized medicament, may flow. The tube 90, 290 defines an inlet 92, 292 to the cavity 32, 272, with inlet 92 being in fluid communication with only the upper nasal cavity 64 of the mask 24, or with the cavity 72, 272 of nasal mask 26, 200. An annular flange 295 extends radially outwardly from the tube 290, and may define a stop member in one embodiment as explained in more detail below. The edge portions of the mask are configured with a flexible sealing edge 94, formed by an inwardly curved lip of the mask, which mates with the chin, cheeks and nose of the user in the embodiment of FIGS. 1-3, or with the upper lip and nose of the user in the embodiments of FIGS. 4A-13. The sealing edge 94 may be made of soft seal silicone, which may be overmolded on a front portion of the shell, also made of silicone, as shown in FIG. 13, or be integrally formed therewith as shown in FIG. 16. The sealing edge may have a width of about 10 mm. The various features and components of the mask may be made of various materials, including silicone rubber, ABS, liquid silicone rubber, and/or PBT.

Referring to FIGS. 1-3 and FIGS. 4A-23, the mask is configured with a one-way exhaust valve assembly 96 in the bottom wall portion defining in part the lower oral cavity, while the nasal mask is configured with a one-way exhaust valve assembly 96, 296 in the bottom wall portion defining in part the cavity. In one embodiment, the valve assembly is configured as a flap valve covering one or more exhaust ports 98, 298 (shown as two) formed in the bottom wall portion of the shell, although the valve may be configured as a center opening annular donut valve, a slit valve, a center-post valve, or other know and suitable valve configurations.

In the embodiment of FIGS. 14-23, the valve assembly 296 includes a valve seat 302 defining the exhaust ports 298 and a valve 306, configured with a pair of flaps 308 that may pivot relative to a center portion defining a centerline, coupled to the body with a tether 310, or other flexible member. The tether 310 extends from the center portion along one edge (e.g., bottom) of the valve, and may have a thinned region defining a living hinge, permitting the valve to be pivoted about an axis defined by the living hinge (e.g., for cleaning) while remaining tethered to the mask. The valve may be made of silicone, and may have a thickness, for example and without limitation, of between and including 0.15 to 0.60 mm. The valve 306 includes a post 304 extending from the center portion, while the seat defines a pair of ports 298 and a center opening 314. The post 304 is inserted into the opening 314 and is secured thereto with a friction fit, or with a catch or detent, such that the flaps 308 may pivot or move away from the ports 298 during exhalation, but seal against the valve seat 302 around the ports 298 during inhalation, with the valve assembly 296 thereby defining a one-way exhalation valve. It should be understood that the valve may be a one-piece molded component pre-assembled with the mask.

In the embodiment of FIGS. 1 and 2, the mask is also configured with a one-way exhaust valve 100 in one of the side wall portions defining in part the upper nasal oral cavity. In one embodiment, the valve 100 is configured as a center post valve having a peripheral edge that moves away from a circumferential valve seat 104. A valve hub 102 is connected to the seat with spokes 106, which define exhaust ports 108 therebetween, with a center post of the valve secured in the hub. It should be understood that the valve may be configured as a flap valve, a center opening annular donut valve, a slit valve, a center-post valve, or other know and suitable valve configurations.

As shown in the embodiment of FIG. 3, the mask is not configured with an exhaust valve communicating with the upper nasal cavity. The exhaust valves 96, 100 allow the user to breath in and out, or complete repeated breathing cycles, without having to remove the mask from their nose or face. Air may also be exhausted through an exhaust valve 19 located on the holding chamber, solely or in combination with the exhaust valve(s) located on the mask. In some embodiments, the mask body does not include any exhaust valves, but rather exhalation gases are passed through the inlet 92 and out through the medicament delivery device, for example through the exhaust valve 19 of the holding chamber, or the user simply exhales through their mouth when using the nasal mask.

Referring to FIGS. 4A-23, the mask is configured with various embodiments of a therapeutic substance dispenser 110, 210, 410 which holds for example a therapeutic component 112, 114, 116, 118, 119 and dispenses a therapeutic substance, which may be configured as and including a medication, for example an aerosolized nasal aromatic decongestant that has an aroma, or pleasant and distinctive smell. The therapeutic component and substance may be configured as an aromatic component and substance alone, a combined aromatic component and substance and medication (e.g. decongestant), or a medicament such as a decongestant without an aroma. One suitable aromatic nasal decongestant component is a Vicks® VapoInhaler™ inhaler stick 112, or Vicks® VapoPatch™ patches, which includes an aromatic nasal decongestant, and emits an aromatic nasal decongestant substance. The therapeutic component may also be configured as an aromatic crystal 119, shown for example in FIG. 20C.

Figure 4A:
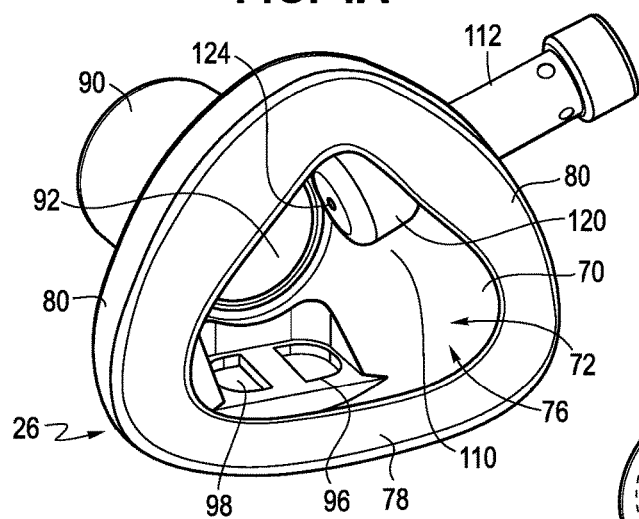
FIGS. 4A and B are perspective views of one embodiment of a mask in solid and see-through configurations.
Figure 4B:
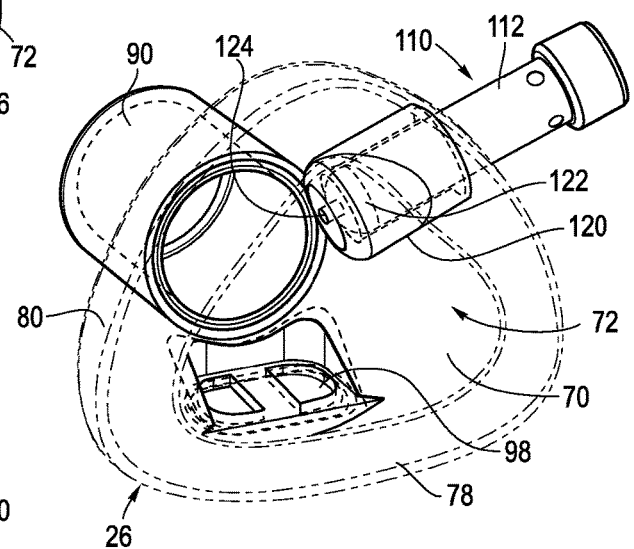

Referring to FIGS. 4A-4B, the dispenser 110 includes a receptacle 120 that extends partially interiorly into the cavity 72, but does not interfere with the user's nose during use. The receptacle 120 defines an interior cavity 122 or reservoir that is in direct fluid communication with the upper nasal cavity 64 of the mask or the cavity 72 of the nasal mask at a location spaced apart from the inlet 92, and downstream (during inhalation) thereof. The location of the communication is also spaced apart from the exhaust valve 96, 100. It should be understood that the receptacle may be configured in other locations on the mask, including for example on the tube 90 or in communication with the inlet 92, or in or on a medicament delivery device upstream (during inhalation) of the inlet. For example, as shown in the embodiments of FIGS. 14-23, a receptacle 412 communicates with the cavity 272 adjacent the inlet 292, and along/around a periphery 414 thereof. In one embodiment, shown in FIGS. 5A and B, the receptacle has an orifice 124, 424 that opens directly into the cavity 64, 72, 272 and is in direct fluid communication between the cavities 122, 64, 72, 272 at a location spaced apart from the inlet, and downstream (during inhalation) thereof. The orifice is positioned or spaced above a bottom of the cavity 122 a distance "d" (see FIG. 5B) such that the therapeutic component does not block the orifice or leak out of the orifice and into the cavity 64, 72 of the mask, but rather is diffused or entrained in the air passing through the orifice 124, which provides for a fluid communication of the therapeutic component with the cavity 64, 72.

In one embodiment, the orifice 124, 424 has a diameter between and including 1 mm and 7 mm. The orifice 124, 424 may have a non-circular cross-section, with a cross-sectional area of between and including 0.78 mm² and 39 mm². The size of the orifice 124, 424 ensures a slow release of the therapeutic substance, such as an aromatic decongestant substance, during inhalation in order to provide a pleasant experience to the user. In the embodiment of FIGS. 4A-4B, the inhaler stick 112 is inserted into the cavity 122 of the receptacle. The therapeutic substance, such as the aerosolized nasal decongestant, may pass through the orifice 124 and into the cavity 64, 72, either through natural diffusement into the air or by entrainment with air passing through the inhaler stick and/or cavity 122 during a user breathing cycle. The cavity 122 has a cylindrical shape to accommodate the stick 112, although it should be understood that other shapes would also work.

Figure 5A:
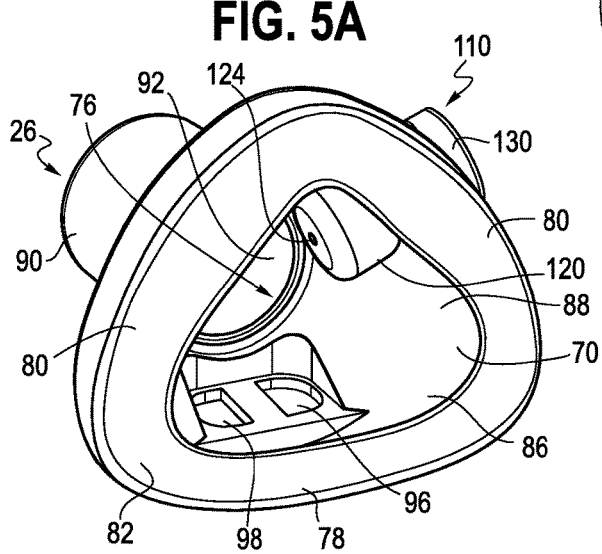
FIGS. 5A and B are perspective views of another embodiment of a mask in solid and see-through configurations.
Figure 5B:
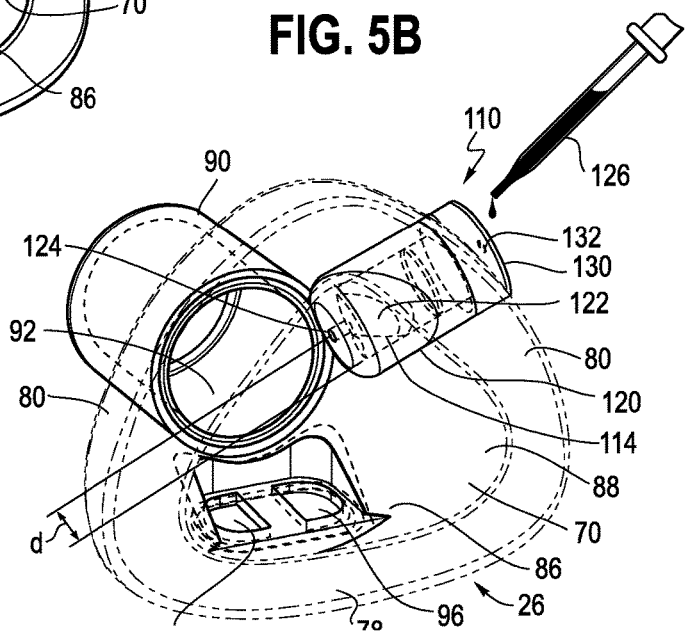

Referring to FIGS. 5A and B, the therapeutic component may be configured as a liquid 114, which may be deposited in the receptacle reservoir or cavity 122, for example with an eye dropper 126, bottle or other dispenser. The end of the reservoir may be open to the ambient environment, or closed with a plug 130 or cap having a second orifice 132 allowing for air flow or fluid communication between the cavity 122 and the ambient environment such that entrainment may occur. The second orifice 132 may be same size as the first orifice 124, or a different size, e.g. smaller or larger. The therapeutic substance, such as an aromatic nasal decongestant, may pass through the orifice 124, either through natural diffusement into the air or by entrainment with air passing through the reservoir 122 from the second orifice 132 during a user breathing cycle.

Figure 6A:
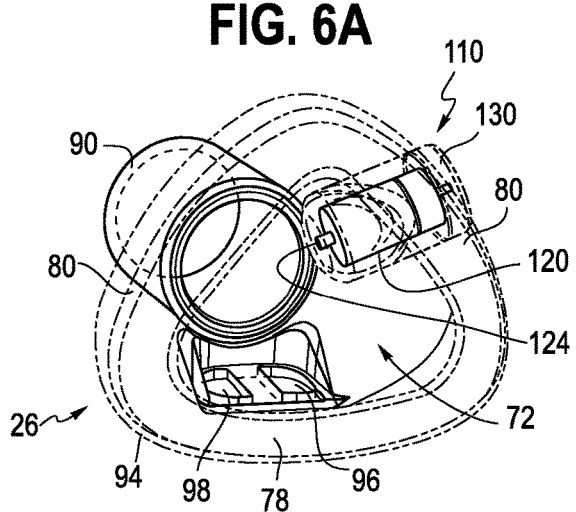
FIGS. 6A and B are left and top perspective views of another embodiment of a mask.
Figure 6B:
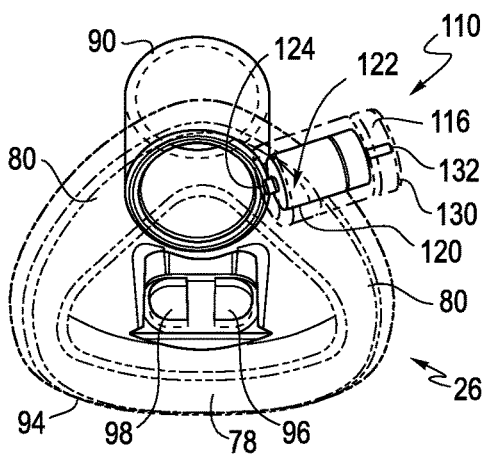

Referring to FIGS. 6A and B, the plug 130 may be impregnated with a therapeutic component 116, such as a liquid. The plug, which may include an orifice 132, is inserted into the cavity 122. The therapeutic substance, such as an aromatic nasal decongestant, may pass through the orifice 124 and into the cavity 64, 72, either through natural diffusement into the air or by entrainment with air passing through the cavity 122 during a user breathing cycle.

Figure 7A:
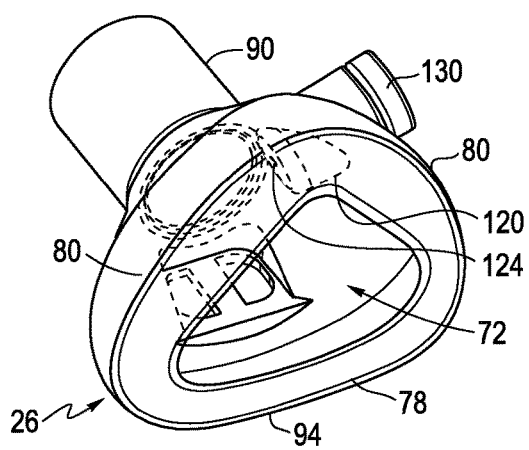
Figure 7B:
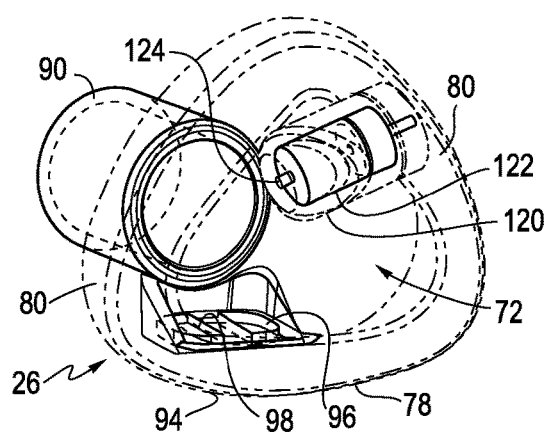
Figure 7C:
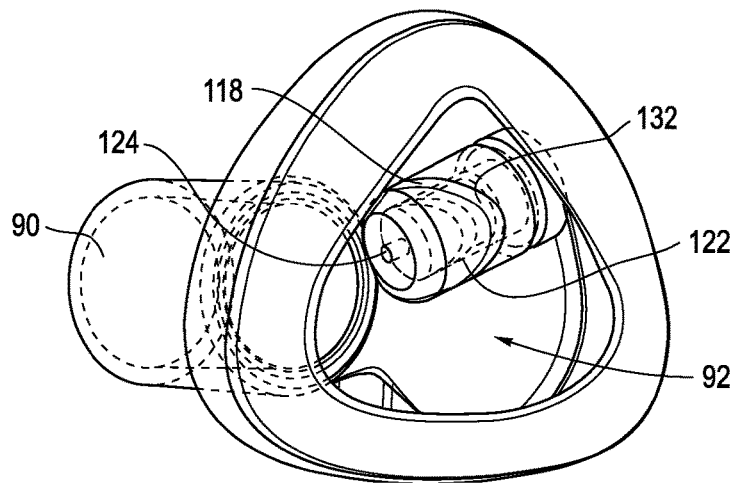
FIG. 7C is an enlarged view of an aromatic dispenser.
Figure 8A:
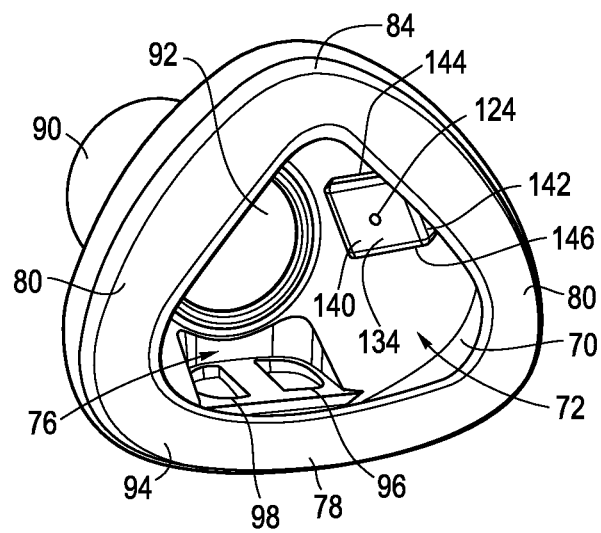
FIGS. 8A, B and C are a perspective and side views of another embodiment of a mask.
Figure 8B:
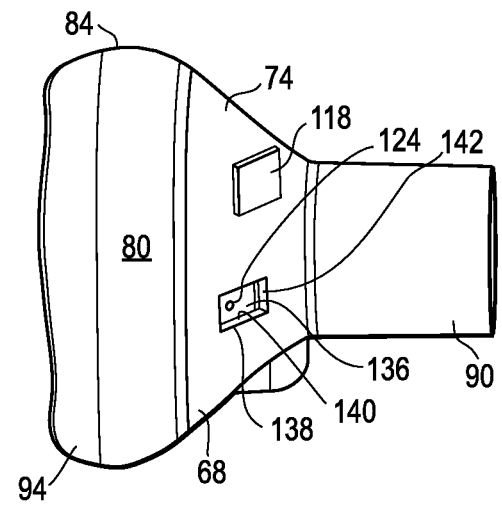
Figure 8C:
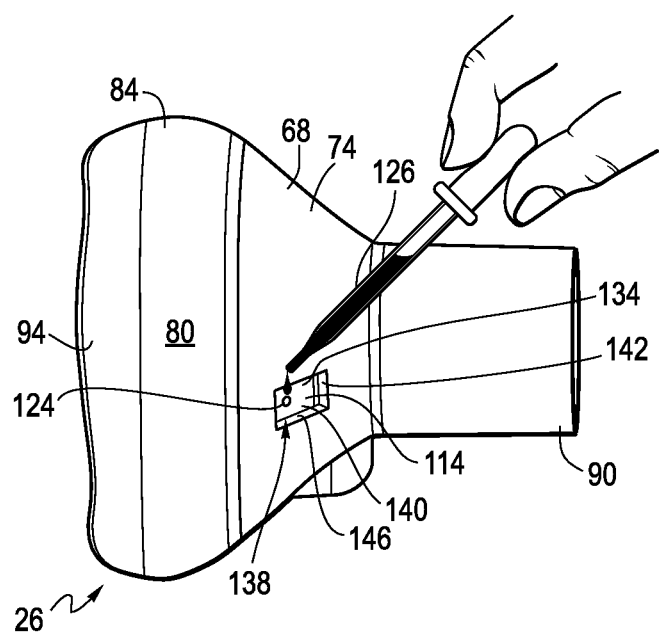
Figure 9:
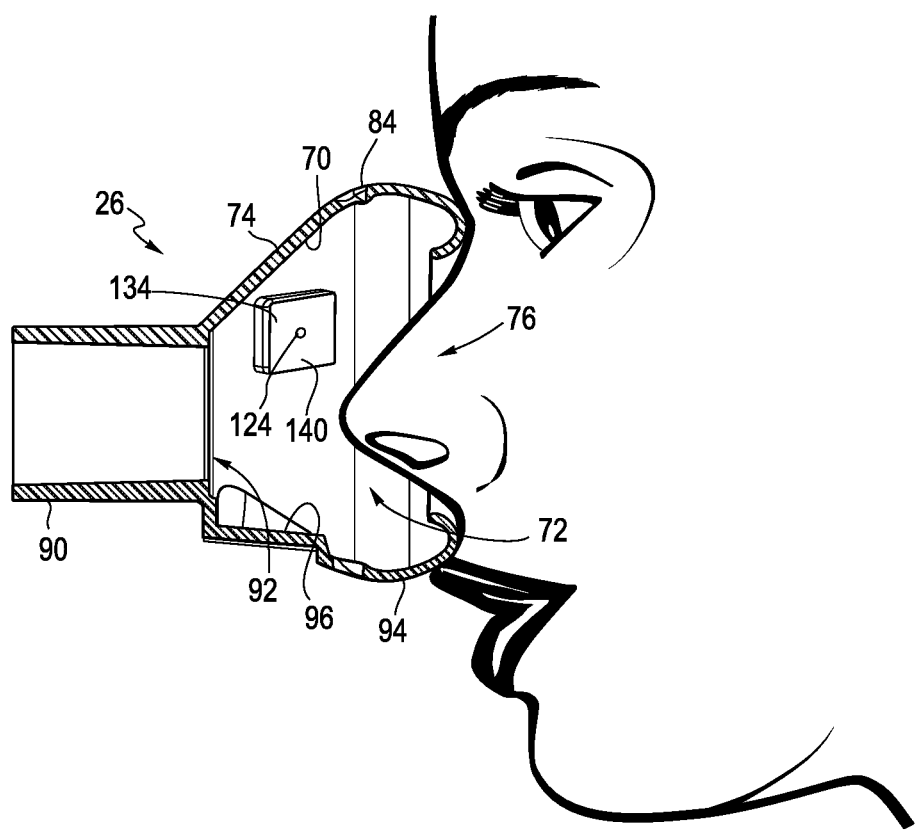
FIG. 9 is a side view of one embodiment of a nasal mask in use.

Referring to FIGS. 7A-C, a therapeutic component strip 118, e.g., an aromatic decongestant strip, is disposed in the cavity 122, which may be left open, or closed with a plug 130 or cap having an orifice 132. Again, the therapeutic substance, such as an aromatic nasal decongestant, may pass through the orifice 124 and into the cavity 64, 72, either through natural diffusement into the air or by entrainment with air passing through the cavity 122 during a user breathing cycle.

Referring to FIGS. 8A-C and 9, a receptacle 134 is configured with a cavity 136 having an access window 138 exposed to the ambient environment. In one embodiment, the cavity has a rectangular shape defined by side walls 142 and upper and bottom walls 144, 146, with an orifice 124 extending through an interior wall 140 and communicating the cavity of the mask. Again, the orifice is spaced above the lower wall 146. The therapeutic component, such as a liquid 114 or strip 118, may be deposited in the cavity, for example with an eye dropper 126, bottle or other dispenser. The therapeutic substance may pass through the orifice 124 and into the cavity 64, 72, either through natural diffusement into the air or by entrainment with air passing through the cavity during a user breathing cycle.

Referring to FIGS. 1-3 and 10A-11, the receptacle 150 is formed on the interior of the cavity 72 and is in fluid communication therewith, but is not in fluid communication with the ambient environment. The receptacle defines a cavity 152 or reservoir, and may be configured for example as a pouch having a front wall 154, a pair of side walls 156 and a bottom wall 158, with a rear wall 160 defined by the side wall of the shell. The cavity 152 is open to the top of the receptacle 134. The front wall has one or more openings 162 defining a grid, with a bottom of the openings 162 being spaced upwardly from the bottom wall 158, such that the therapeutic component 114, 118 is retained in the cavity. The therapeutic substance, such as a nasal decongestant, may pass through the openings 162 in the front wall, or through the open top 164, to the cavity of the nasal mask or to the upper nasal cavity, for example through natural diffusement into the air or by entrainment with air passing through the cavity during a user breathing cycle, for example air entering through the open top 164 and out of the openings 162, or air entering in through one of the openings and out through one or more openings or the open top 164. The therapeutic component, such as a liquid 114 or strip 118, may be deposited in the cavity 152, for example with an eye dropper 126, bottle, tweezers or other dispenser.

Referring to FIGS. 14-23, the therapeutic substance dispenser 210, including receptacle 412, is in fluid communication with the cavity 272 adjacent the inlet 292, and preferably along or about a periphery 414 of the inlet. The receptacle 412 includes a cavity 416 formed along a portion of an inner periphery of the tubular mounting portion and is defined in part by the inner surface 291 of the tubular mounting portion. In one embodiment, the receptacle includes a pair of circumferentially spaced cavities 416 formed along portions of the inner periphery of the tubular mounting portion. In other embodiments, the receptacle may include only a single cavity, or may include more than two cavities. Each cavity includes a front/downstream wall 418 having at least one orifice 424 formed therein. In one embodiment, the wall includes five orifices, although a central one of the orifices may be used as an anchor hole for receiving an anchor post of a one-way valve coupled to the wall. In one embodiment, each orifice 424 has a diameter between and including 1 mm and 7 mm, and may have a non-circular cross-section, with a cross-sectional area of between and including 0.78 $mm^2$ and 39 $mm^2$.

Figure 21:
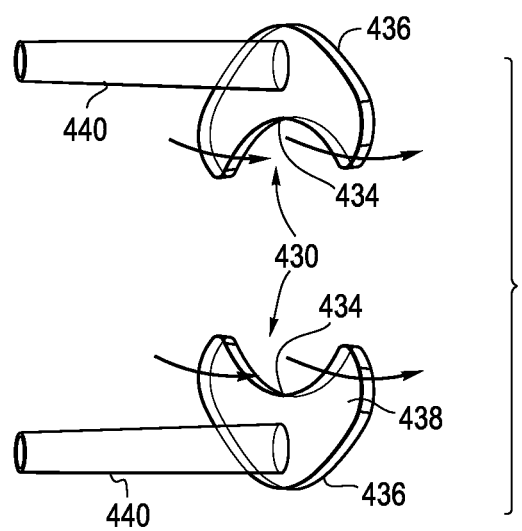
FIG. 21 is a perspective view of a pair of dispensing valves.
Figure 22A:
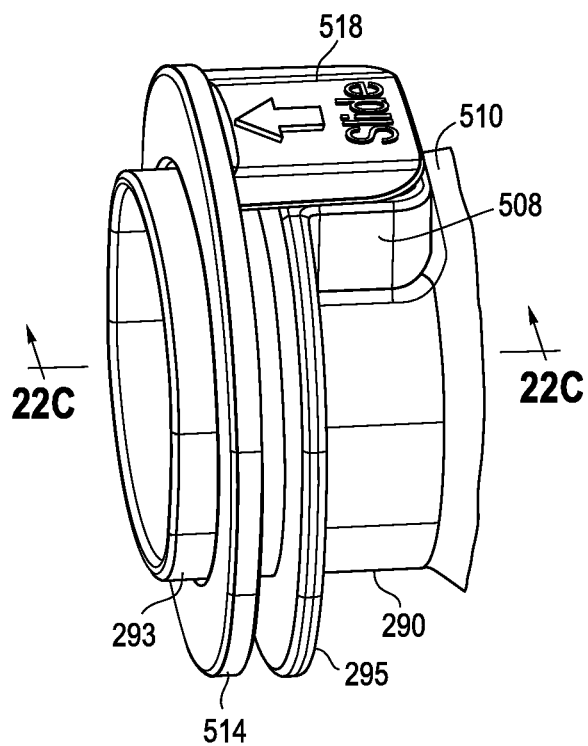
FIGS. 22A and B are side and cross-sectional views of a portion of the mask in an open or use configuration.
Figure 22B:
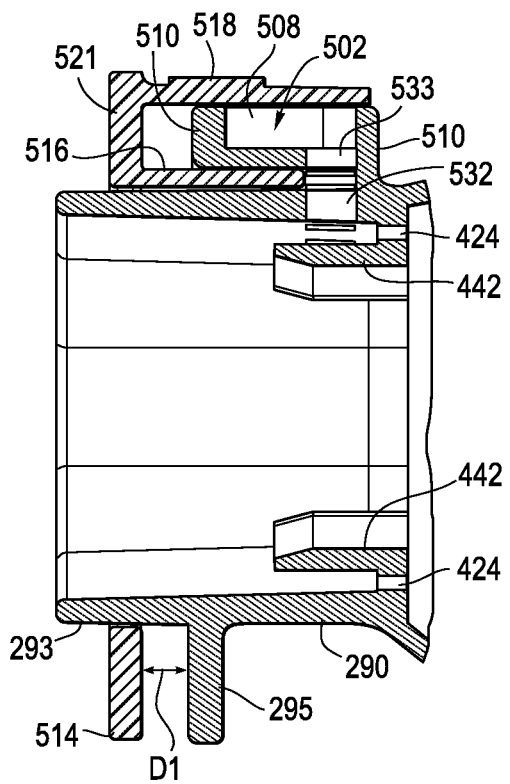
FIG. 22C is a cross-section view of a portion of the mask in the open or use configuration with a medicament disposed therein.
Figure 22C:
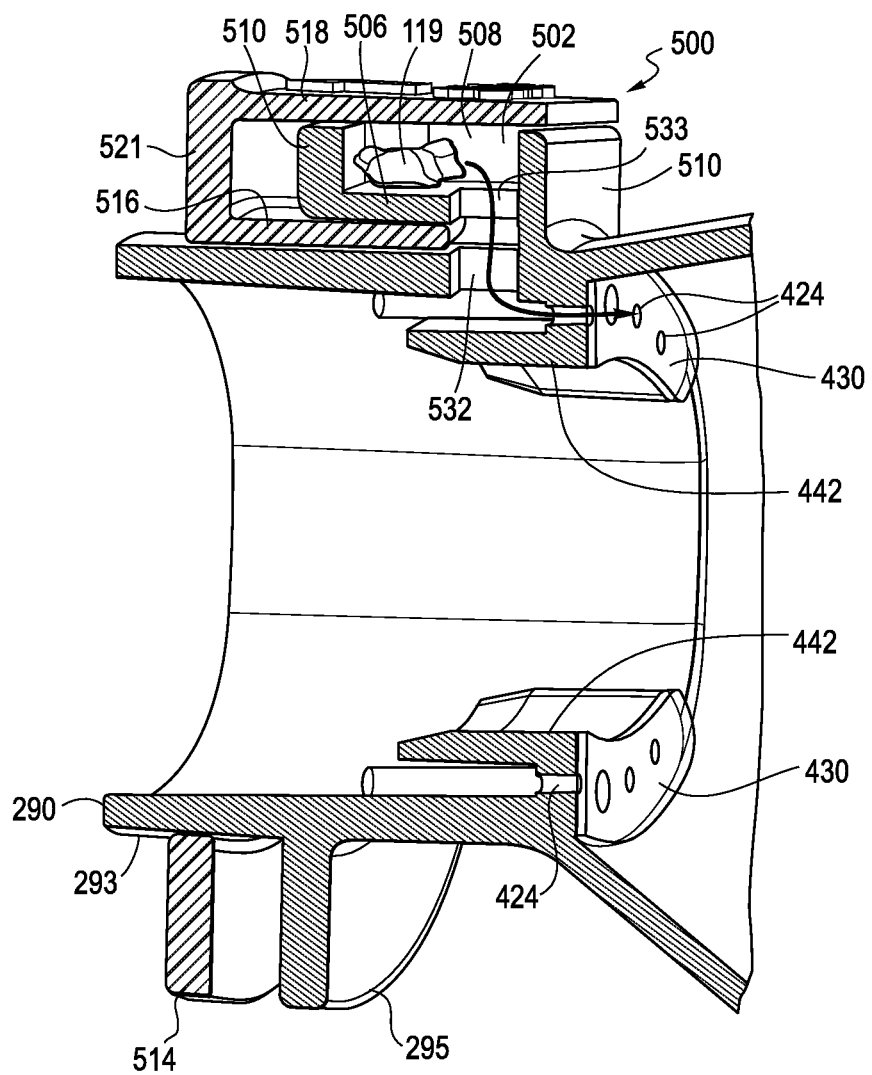

As shown in FIG. 21, a pair of one-way valves 430 each include a planar flap 432 having a curved shape defined by a concave inner edge 434 and a convex outer edge 436, with the anchor post 440 extending orthogonally from the flap along a centerline thereof closer to the outer edge than the inner edge. The flap, including end portions 438 thereof and the inner edge 434, may twist or deform in response to a flow through the orifices 424, moving between a closed position, wherein the flap 432 covers the orifices 424, and an open position, wherein one or more of the orifices 424, or portions thereof, are not covered by the flap 432. The anchor post 440 may have a radially enlarged portion (e.g., mushroom head) that frictionally engages the interior wall of one of the orifices to locate the valve 430 over the orifices 424. Airflow through the valved holding chamber and mask creates a low pressure region that opens the valves 430, which are very thin (e.g., 0.15 to 0.60 mm). When closed, the valves 430 limit the release of the decongestant aroma, for example on demand when a low pressure region is created by inhalation. It should be understood that the valves 430 are optional, meaning the mask maybe configured without the valves, with the aroma from the decongestant being freely dispersed due to airflow through the mask.

The cavity 416 is further defined by an annular, curved wall 442 spaced apart from the wall defining the tubular mounting portion. A free end of the wall 442 may be tapered, or include a ramped surface to engage an exterior surface of the mouthpiece 18. The curved wall extends rearwardly in an upstream direction from the downstream front wall 418. The annular wall and tubular mounting portion define a mouth 446 of the cavity therebetween. A pair of side walls 444 extend between the annular wall and tubular mounting portion to further close off and define the cavity.

The mouthpiece 18 is inserted into the tube 290, with an outer surface of the mouthpiece engaging the inner surface of the wall 442 and the inner surface 291 of the tube 290 and thereby further defining the receptacle and cavity 416 as shown in FIGS. 15-17B. The mouthpiece 18 seals against the tube 290, thereby preventing ambient air (outside of the mask and valved holding chamber) from entering (or exiting) the flow path defined by those components. Air, however, may make its way into the cavity 416 to entrain the therapeutic substance 118 as air passes from the cavity 416 through the orifice(s) 424 as the flap opens 432 in response to the flow during inhalation and into the cavity 272, whereinafter it may be inhaled by the user through the opening 276. In particular, air flows upstream from the mask cavity 272 though a passageway defined between the outer surface of the end of the mouthpiece 18 and the inner surface 291 of the tube at a location downstream from where the mouthpiece 18 and tube 290 are sealed, for example through a gap formed between the side of the mouthpiece 18 and a side portion of the inner surface 291 of the tube between the sidewalls 444 defining the top and bottom cavities 416. The air circles around the edges of the sidewalls 444 and curved wall 442 and into the cavity 416 thereby passing by and entraining the therapeutic substance whereinafter the air exits the orifice(s) 424 as the flap 432 opens.

Referring to FIGS. 18A-22C, a receptacle 500 defines a cavity 502 having a general open top 504 that is open to the ambient environment. The receptacle has a bottom wall 506 spaced apart from an exterior or outer surface 293 of the tubular portion, and defining a gap 522 therebetween. The receptacle further includes a pair of side walls 508 and a pair of end walls 510 connected to the side wall to define a bowl.

Figure 20A:
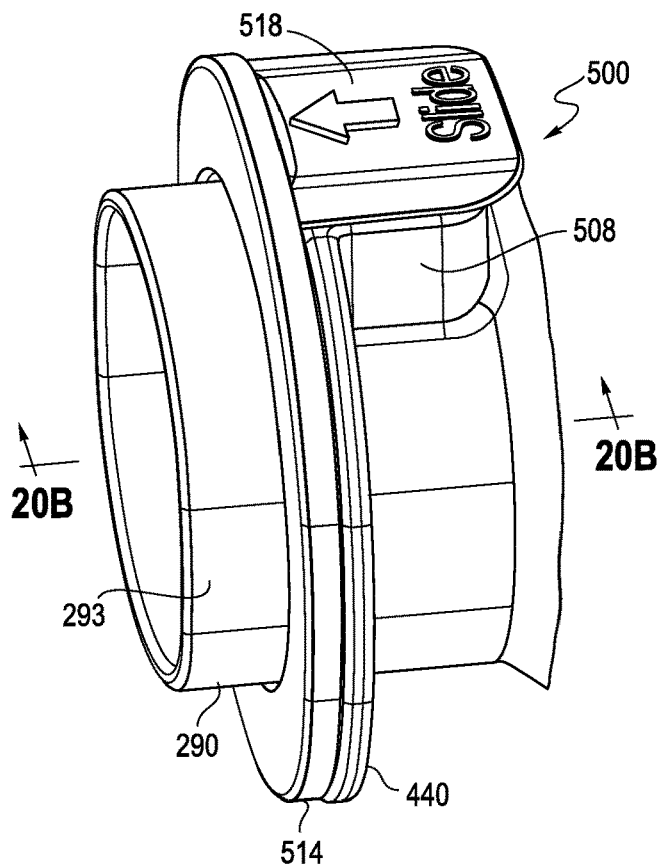
FIGS. 20A and B are side and cross-sectional views of a portion of the mask in a closed or storage configuration.
Figure 20B:
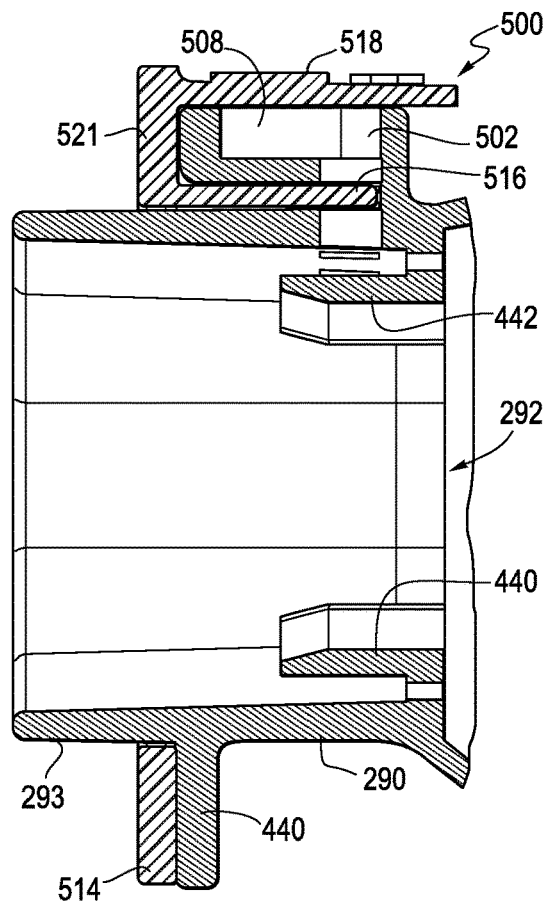
FIG. 20C is a cross-section view of a portion of the mask in the closed or storage configuration with a medicament disposed therein.
Figure 20C:
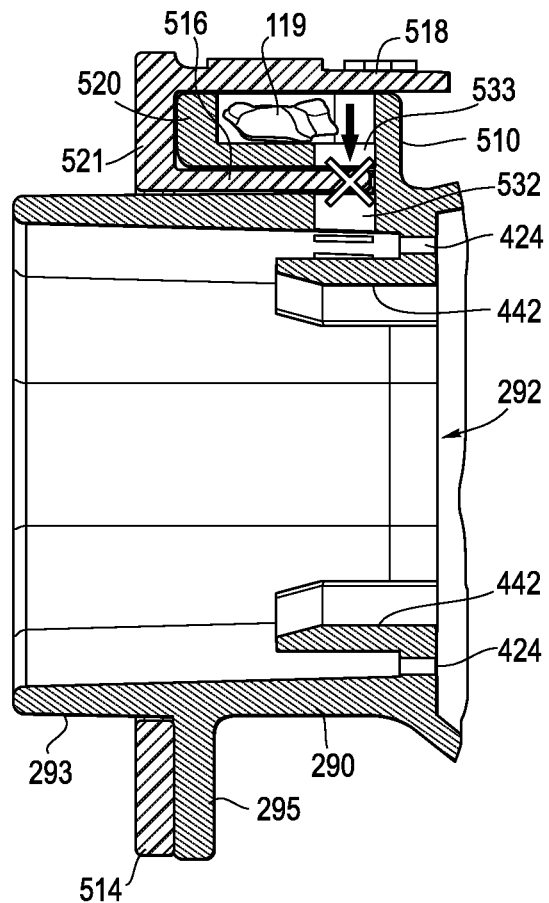

A cover 512 includes a ring 514 that surrounds or is disposed around and axially slidable along the outer surface 293 of the tubular mounting portion 292 extending from the body. The cover further includes first and second cover portions 516, 518, configured as panels or lids, that are spaced apart and form a gap 520 therebetween. The lower panel 516, or first cover, is dimensioned to be received in the gap 522, with the receptacle 500 disposed in the gap 520 between the panels 516, 518, while the upper panel 518, or second cover, is disposed over the top 504 of the receptacle. The cover 512 may be moved, including translating or sliding the cover in a longitudinal direction 530 relative to the tubular mounting portion and receptacle. The first cover portion is moveable relative to a passageway 532 defined between a bottom surface of the bottom wall 506 of the receptacle 500 and the at least one orifice 424. The passageway 532 includes a plurality of ports 533 opening in the bottom of the cavity 502. The cover 516 may move between a first position, wherein the ports 533 are uncovered and the passageway 532 is open, and a second position, wherein the ports 533 are covered and the passageway 532 is closed. In this way, the cover 512 is movable between a use position (FIGS. 22A-C), wherein the cavity 502 is in fluid communication with the orifice 424 by way of the ports 533 being uncovered and the passageway 532 being open, and a storage position (FIGS. 20A-C), wherein the cavity 502 is not in fluid communication with the orifice 424 by way of the ports 533 being covered and the passageway 532 therefore being closed. The cover 512 is further moveable to a loading position (FIGS. 19A and B), wherein the receptacle 500, and in particular the top 504 thereof, is open to the ambient environment. The ring 514 abuts a rear surface of the flange 295 in the storage position as shown in FIGS. 20A-C, is spaced apart from the flange 295 a first distance D1 in the use position (FIGS. 22A-C) and is spaced apart from the flange a second distance D2 in the loading position (FIGS. 19A and B), with D2 being greater than D1. In the loading position, an aromatic crystal 119, or other therapeutic substance such as a decongestant, may be disposed or loaded into the cavity 502. The cover 512 may then be moved to a storage position, wherein the receptacle 500 is not open to the ambient environment. It should be understood that in the storage position, there receptacle is not hermetically sealed, or air tight, meaning some air may enter the receptacle through various gaps between the cover 512 and receptacle 500, but that the open top 504 of the cavity is generally covered and closed such that the therapeutic substance may not fall out or be dislodged. The first and second cover portions 516, 518 are fixedly coupled by way of a rear wall 521, which is configured as a portion of the ring 514 in one embodiment, and are moveable with each other between the loading, storage and use positions.

It should be understood that the masks of FIGS. 1-3 may incorporate and include any of the therapeutic dispenser embodiments disclosed and shown in FIGS. 4A-23.

In operation, the medicament delivery device is positioned such that the nasal mask 26, 200 or the upper nasal cavity 64 surrounds or overlies the nasal passageways of the user. When situated in these configurations, the user may breath normally through their nose 170 and nasal passageways, with air and an inhalable substance flowing through the medicament delivery device, for example through the output end 12 as the inhalation valve 16 opens, through the inlet 92 and into the open space defined by the cavity 72, 64. The inhalable substance, such as an aerosolized medicament, may be dispensed by actuating the pressurized metered dose inhaler 10. For example, the container 174 of a MDI may be reciprocally moved relative to an actuator boot 172 so as to release a metered dose of aerosolized medicament through the mouthpiece 176 coupled to the inlet. The medicament is drawn into the mask 24, 26, 200 wherein the aerosolized medicament is inhaled by the user. The device may be actuated one or more times as needed and prescribed. The medicament or other inhalable substance, such as oxygen and/or an aromatic substance in vapor form, may be administered by a metered dose inhaler or nebulizer, and may be positioned in a ventilator circuit, or other system providing an oxygen supply.

Prior to, or at the same time, the inhalable substance is being administered, a therapeutic component 112, 114, 116, 118, 119 is disposed in the receptacle, with a therapeutic substance being drawn into the cavity 64, 72, 272 through diffusement into the air or by entrainment during inhalation and thereafter drawn into the nose or nasal passageways.

During exhalation, the air passes back through the cavity 72, 64, 66, 272 and through one or both of the exhaust valve assemblies 96, 100, 296. During inhalation, the one-way exhalation valves 96, 100, 296 are closed, while during exhalation, the one-way inhalation valve 16 is closed, thereby creating a back-pressure and forcing the exhaled gases out through the one or more one-way exhaust valves 96, 100, 296, or through an exhaust valve in the medicament delivery device such as the holding chamber 4. The caregiver, whether the provider soothing the user, or a third party observer, may monitor the exhaust valves or flow indicator 22, and in particular the movement thereof, to confirm the patient is exhaling. Movement of the exhaust valves may also provide information about the quality of the seal between the mask and the user's face.

Referring to FIGS. 18A-22C, the cover 512 is moved to the loading position, wherein the receptacle 500 is open to the ambient environment. The therapeutic substance 119, e.g. an aromatic crystal or other decongestant material, is disposed or loaded into the cavity 502. The cover 512 is thereafter moved to a storage position, wherein the receptacle 500 is not open to the ambient environment or in flow communication with the cavity 272, and the cover 512 prevents the aromatic crystal or other decongestant material from falling out of the receptacle, for example when transporting or storing the mask and/or holding chamber. When it is time to administer a medicament, for example when the patient is notified by the device or through a Smart device, the cover 512 is moved from the storage position to the open/use position, for example by translating or sliding the cover in the longitudinal direction 530 relative to the tubular mounting portion 290 and receptacle 500, and thereby exposing the ports 533 and passageway 532, which is closed by the cover 512 in the storage position. In the open/use position, the cavity 502 is in fluid communication with the orifice 424 by way of the passageway 532 being open. The user may thereafter inhale through the mask, and thereby draw the therapeutic substance into the cavity 272 through the orifice(s) 424 past the open valve 430 by way of diffusement into the air flow and/or by entrainment during inhalation, and thereafter draw the therapeutic substance into the nose or nasal passageways from the cavity 272.

Referring to FIGS. 14-23, the valve post 304 may be removed from the center opening 314, while the valve 306 remains tethered to the mask, such that the valve may be pivoted away from the valve seat 302 to a disengaged position, whereinafter the valve, valve seat and mask may be cleaned. The valve may be reengaged with the valve seat by inserting the post 304 into the opening 314 and engaging the mask. Preferably, the valve 306 remains tethered to the mask with the tether, configured as a living hinge, at all times such that the valve is not misplaced.

Figure 23:
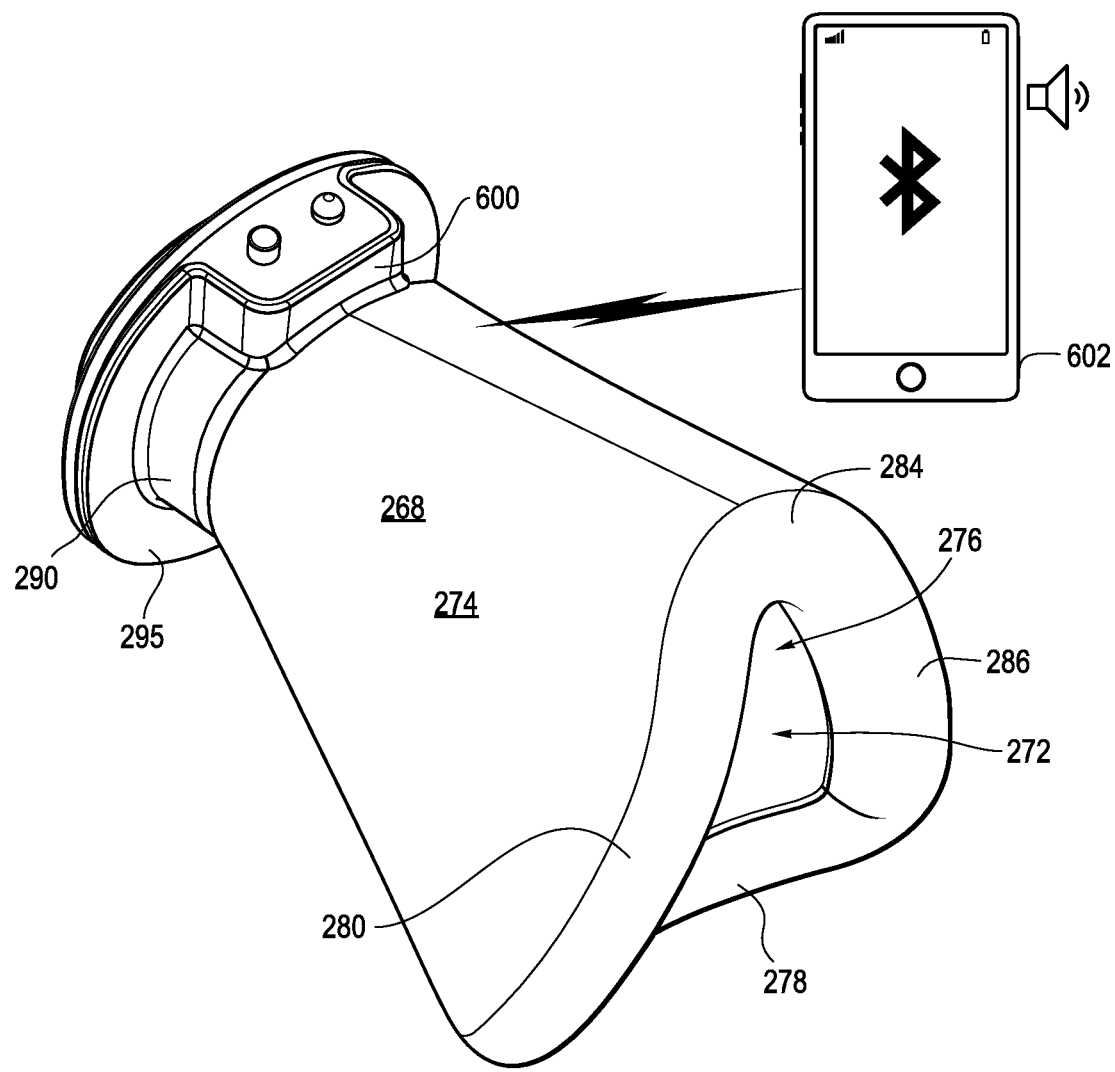
FIG. 23 is a perspective view of a mask with a controller.
Figure 24:
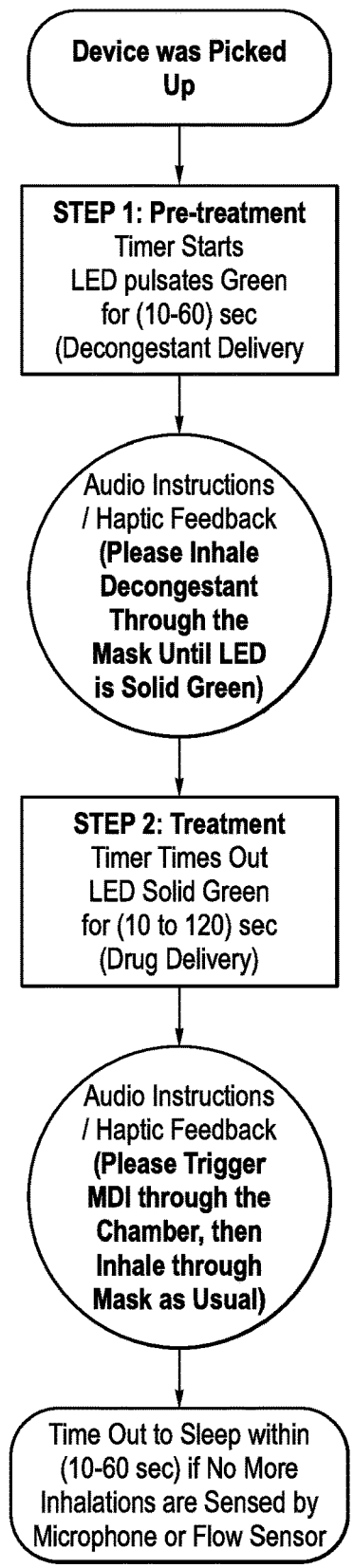
FIG. 24 is a flow chart illustrating the operation of the controller shown in FIG. 23.

Referring to FIGS. 23 and 24, the mask may be configured with a controller 600, for example coupled to the mounting portion. The controller 600, or other component of the mask, may include a microprocessor, a microphone, a flow sensor in fluid communication with, or capable of sensing the flow in, the flow path, a speaker and/or a haptic feedback feature, for example a vibrator. The controller, or other component of the mask, may also include a volatile organic compound (VOC) sensor. VOC's are gases that are emitted into the air from products or processes, for example from the decongestant. The VOC sensor measures the concentration of the aromatic decongestant, with the concentration of the decongestant being tracked and logged by an application. Specifically, the VOC sensor measures the ambient concentration of a broad range of "reducing gases," for example and without limitation, alcohols, aldehydes, ketones, organic acids, amines, organic chloramines, aliphatic and aromatic hydrocarbons. If a decongestant intensity limit falls below a specific predetermined level, or pre-set limit, the controller, via the application, will communicate a reminder to the user, for example through a user interface 602, or by way of indicators located on the mask, providing indicia or instructing the user to replace the therapeutic substance, or decongestant component, with a fresh supply, e.g., stick, pad, crystal, etc. In one operation sequence, a timer informs the user to breathe the therapeutic substance, or decongestant, in/out through the mask before the medicament or drug treatment in order to open the nostrils as a pre-treatment. In operation, the user would pick up the mask 200, whether separate or attached to a medicament delivery device such as a holding chamber, press a first button A to start the clock, with LED lights/indicators B pulsating green while counting down a predetermined "pretreatment" time period, after which the device is ready for the medicament delivery treatment. When the pre-treatment is completed the LED indicator B would turn to solid green to indicate that drug can now be administered. The solid green LED indicator B will then timeout after a few seconds after the medicament treatment sequence is completed or finished.

In another embodiment, following an automatic solution sequence, a timer informs the user to breathe decongestant in/out through the mask 200 before the drug treatment in order to open the user's nostrils as a pre-treatment. The user would pick up the mask 200, with an accelerometer sensor automatically starting a timer or countdown clock and with the LED indicator B lighting up in a pulsating green count down mode signaling the device is ready for pre-treatment. When the pre-treatment is completed, the LED indicator B would turn to solid green to indicate that drug may be administered. The LED indicator B will then timeout after a few seconds after the drug delivery treatment is finished. In one embodiment, a user interface 602, including without limitation one or more of a smart phone, tablet or computer, may connect to the controller 600 via Bluetooth, allowing the user to interface with the user interface 602 and initiate the operation sequence for pretreatment and treatment and receive feedback about the treatment. As set forth in FIG. 24, the mask 200 and controller 600, for example through the speaker(s), may provide audio instructions about how to use the device and proceed with treatment.

In various embodiments, the inhalable substance is an aerosolized medication that may be administered using the medicament delivery assembly and device, which medication may include, without limitation, corticosteroids, such as beclamethasone, budesonide, flunisolide, cilcesonide, and fluticasone, and bronchodilators, such as albuterol, proventil, levalbuterol, salmeterol and pirbuterol.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A mask comprising:
  a body comprising:
    an interior surface defining a cavity shaped to receive a user's nose;
    an exterior surface exposed to an ambient environment;
    an inlet in fluid communication with and opening directly into the cavity; and
    a therapeutic substance dispenser comprising at least one orifice in fluid communication with and opening directly into the cavity, at a location spaced apart from the inlet; and
  a tubular mounting portion extending from the body and having an upstream end adapted to receive an output member of a medicament delivery device and a downstream end defining the inlet.

2. The mask of claim 1 wherein the therapeutic substance dispenser comprises a receptacle in fluid communication with the cavity via the at least one orifice.

3. The mask of claim 2 wherein the at least one orifice communicates between the receptacle and the cavity.

4. The mask of claim 3 wherein the at least one orifice has a diameter between and including 1 mm and 7 mm.

5. The mask of claim 3 wherein the at least one orifice comprises a plurality of orifices.

6. The mask of claim 2 wherein the receptacle is integrally formed with the mask body or the tubular mounting portion.

7. A mask comprising:
  a body comprising:
    an interior surface defining a cavity shaped to receive a user's nose;
    an exterior surface exposed to an ambient environment;
    an inlet in fluid communication with and opening directly into the cavity; and
    a therapeutic substance dispenser comprising at least one orifice in fluid communication with and opening directly into the cavity at or downstream of the inlet, wherein the therapeutic substance dispenser comprises a receptacle in fluid communication with the cavity via the at least one orifice, wherein the at least one orifice communicates between the receptacle and the cavity;
  a one-way valve covering the at least one orifice and movable between open and closed configurations; and
  a tubular mounting portion extending from the body and having an upstream end adapted to receive an output member of a medicament delivery device and a downstream end defining the inlet.

8. A mask comprising:
  a body comprising:
    an interior surface defining a cavity shaped to receive a user's nose;
    an exterior surface exposed to an ambient environment;
    an inlet in fluid communication with and opening directly into the cavity; and
    a therapeutic substance dispenser comprising at least one orifice in fluid communication with and opening directly into the cavity at or downstream of the inlet, wherein the therapeutic substance dispenser comprises a receptacle in fluid communication with the cavity via the at least one orifice, wherein the at least one orifice communicates between the receptacle and the cavity, wherein the cavity comprises a first cavity and wherein the receptacle defines a second cavity;
  a cover movable between a use position, wherein the second cavity is in fluid communication with the at least one orifice, and a storage position, wherein the second cavity is not in fluid communication with the at least one orifice; and
  a tubular mounting portion extending from the body and having an upstream end adapted to receive an output member of a medicament delivery device and a downstream end defining the inlet.

9. The mask of claim 8 wherein the cover is moveable to a loading position, wherein the receptacle is open to the ambient environment.

10. The mask of claim 8 wherein the receptacle is not open to the ambient environment when the cover is in the storage position.

11. The mask of claim 8 wherein the cover is slidable relative to the receptacle.

12. The mask of claim 11 wherein the cover comprises a ring disposed around and axially slidable along the tubular mounting portion extending from the body.

13. The mask of claim 9 wherein the cover comprises a first cover portion moveable relative to a passageway between a bottom of the receptacle and the at least one orifice, and a second cover portion spaced apart from the first cover portion and moveable relative to an open top of the receptacle.

14. The mask of claim 13 wherein the first and second cover portions are fixedly coupled and moveable with each other between the loading, storage and use positions.

15. A mask comprising:
  a body comprising:
    an interior surface defining a cavity shaped to receive a user's nose;
    an exterior surface exposed to an ambient environment;
    an inlet in fluid communication with and opening directly into the cavity; and
    a therapeutic substance dispenser comprising at least one orifice in fluid communication with and opening directly into the cavity at or downstream of the inlet, wherein the therapeutic substance dispenser comprises a receptacle in fluid communication with the cavity via the at least one orifice, wherein the at least one orifice communicates between the receptacle and the cavity; and a tubular mounting portion extending from the body and having an upstream end adapted to receive an output member of a medicament delivery device and a downstream end defining the inlet, wherein the receptacle comprises a cavity formed along a portion of an inner periphery of the tubular mounting portion.

16. The mask of claim 15 wherein the at least one orifice is in fluid communication with and opens directly into the cavity of the interior surface adjacent the inlet.

17. The mask of claim 16 wherein the at least one orifice is in fluid communication with and opens directly into the cavity of the interior surface along a periphery of the inlet.

18. A mask comprising:
a body comprising:
an interior surface defining a cavity shaped to receive a user's nose;
an exterior surface exposed to an ambient environment;
an inlet in fluid communication with the cavity;
a tubular mounting portion extending from the body and adapted to receive an output member of a medicament delivery device; and
a therapeutic substance dispenser in fluid communication with the cavity, wherein the therapeutic substance dispenser comprises a receptacle in fluid communication with the cavity and at least one orifice communicating between the receptacle and the cavity, and wherein the receptacle comprises a pair of circumferentially spaced cavities formed along portions of an inner periphery of the tubular mounting portion.

19. A mask comprising:
a body comprising:
an interior surface defining a cavity shaped to receive a user's nose;
an exterior surface exposed to an ambient environment;
an inlet in fluid communication with the cavity;
a tubular mounting portion extending from the body and adapted to receive an output member of a medicament delivery device; and
a therapeutic substance dispenser in fluid communication with the cavity, wherein the therapeutic substance dispenser comprises a receptacle in fluid communication with the cavity and at least one orifice communicating between the receptacle and the cavity, wherein the receptacle comprises a cavity formed along a portion of an inner periphery of the tubular mounting portion, and wherein the receptacle cavity comprises a downstream wall having the at least one orifice formed therein and an annular wall spaced apart from the tubular mounting portion and extending in an upstream direction from the downstream wall, wherein the annular wall and tubular mounting portion define a mouth of the receptacle cavity therebetween.

20. A medication delivery assembly comprising the mask of claim 19 and a medicament delivery device comprising an output end received in the tubular mounting portion and engaging an inner surface of the annular wall.

21. A mask comprising:
a body comprising:
an interior surface defining a cavity shaped to receive a user's nose;
an exterior surface exposed to an ambient environment;
an inlet in fluid communication with and opening directly into the cavity; and
a therapeutic substance dispenser comprising at least one orifice in fluid communication with and opening directly into the cavity at or downstream of the inlet, wherein the therapeutic substance dispenser comprises a receptacle in fluid communication with the cavity via the at least one orifice, and wherein at least a portion of the receptacle is positioned in the cavity of the body; and
a tubular mounting portion extending from the body and having an upstream end adapted to receive an output member of a medicament delivery device and a downstream end defining the inlet.

* * * * *